(12) United States Patent
Shanmugam et al.

(10) Patent No.: US 9,636,329 B2
(45) Date of Patent: May 2, 2017

(54) METHODS OF TREATING CANCER WITH GLUT INHIBITORS AND OXIDATIVE PHOSPHORYLATION INHIBITORS

(71) Applicant: Northwestern University, Evanston, IL (US)

(72) Inventors: Malathy Shanmugam, Lisle, IL (US); Steven T. Rosen, Chicago, IL (US)

(73) Assignee: Northwestern University, Evanston, IL (US)

( * ) Notice: Subject to any disclaimer, the term of this patent is extended or adjusted under 35 U.S.C. 154(b) by 347 days.

(21) Appl. No.: 14/073,560

(22) Filed: Nov. 6, 2013

(65) Prior Publication Data

US 2014/0142056 A1 May 22, 2014

Related U.S. Application Data

(60) Provisional application No. 61/723,079, filed on Nov. 6, 2012.

(51) Int. Cl.
  *A61K 31/427* (2006.01)
  *A61K 31/155* (2006.01)
  *A61K 45/06* (2006.01)

(52) U.S. Cl.
  CPC .......... *A61K 31/427* (2013.01); *A61K 31/155* (2013.01); *A61K 45/06* (2013.01)

(58) Field of Classification Search
  None
  See application file for complete search history.

(56) References Cited

U.S. PATENT DOCUMENTS

| | | | | |
|---|---|---|---|---|
| 8,084,576 B2 * | 12/2011 | Glover | ................ | A61K 39/0011 530/350 |
| 2008/0176822 A1 * | 7/2008 | Chen | .................... | A61K 31/155 514/162 |
| 2012/0252749 A1 * | 10/2012 | Shanmugam | .... | G01N 33/57484 514/34 |

OTHER PUBLICATIONS

Issa, Z. A., Zantout, M. S., & Azar, S. T. (2011). Multiple myeloma and diabetes. ISRN endocrinology, 2011.*
Iliopoulos, D., Hirsch, H. A., & Struhl, K. (2011). Metformin decreases the dose of chemotherapy for prolonging tumor remission in mouse xenografts involving multiple cancer cell types. Cancer research, 71(9), 3196-3201.*
Evans, J. L., Honer, C. M., Womelsdorf, B. E., Kaplan, E. L., & Bell, P. A. (1995). The effects of wortmannin, a potent inhibitor of phosphatidylinositol 3-kinase, on insulin-stimulated glucose transport, GLUT4 translocation, antilipolysis, and DNA synthesis. Cellular signalling, 7(4), 365-376.*
Bredella et al., "Value of FDG PET in the Assessment of Patients with Multiple Myeloma," AJR Am J Roentgenol, 2005, 184(4): 1199-204.
Carr et al., "A Syndrome of Peripheral Lipodystrophy, Hyperlipidaemia and Insulin Resistance in Patients Receiving HIV Protease Inhibitors," AIDS, 1998, 12(7): F51-8.
Cheong et al., "Dual Inhibition of Tumor Energy Pathway by 2-Deoxyglucose and Metformin is Effective Against a Broad Spectrum of Preclinical Cancer Models," Mol Cancer Ther, 2011, 10(12): 2350-62.
Durie et al., "Whole-Body (18)F-FDG PET Identifies High-Risk Myeloma," J Nucl Med, 2002, 43(11): 1457-63.
El-Mir et al., "Dimethylbiguanide Inhibits Cell Respiration Via an Indirect Effect Targeted on the Respiratory Chain Complex I," J Biol Chem, 2000, 275(1): 223-8.
Evans et al., "Metformin and Reduced Risk of Cancer in Diabetic Patients," BMJ, 2005, 330(7503): 1304-5.
Hertel et al., "A Structural Basis for the Acute Effects of HIV Protease Inhibitors on GLUT4 Intrinsic Activity," J Biol Chem, 2004, 279(53): 55147-52.
Hresko et al., "HIV Protease Inhibitors Act as Competitive Inhibitors of the Cytoplasmic Glucose Binding Site of GLUTs with Differing Affinities for GLUT1 and GLUT4," PLoS One, 2011, 6(9): e25237.
Hsu et al., "Multiple-Dose Pharmacokinetics of Ritonavir in Human Immunodeficiency Virus-Infected Subjects," Antimicrob Agents Chemother, 1997, 41(5): 898-905.
Kohli et al., "A Randomized Placebo-Controlled Trial of Metformin for the Treatment of HIV Lipodystrophy," HIV Med, 2007, 8(7): 420-6.
McBrayer et al., "Multiple Myeloma Exhibits Novel Dependence on GLUT4, GLUT8, and GLUT11: Implications for Glucose Transporter-Directed Therapy," Blood, 2012.
Munshi, "Plasma Cell Disorders: An Historical Perspective," Hematology, 2008, 297.
Murata et al., "The Mechanism of Insulin Resistance Caused by HIV Protease Inhibitor Therapy," J Biol Chem, 2000, 275(27): 20251-4.
Owen et al., "Evidence that Metformin Exerts its Anti-Diabetic Effects Through Inhibition of Complex 1 of the Mitochondrial Respiratory Chain," Biochem J, 2000, 348 Pt 3: 607-14.
Sahra et al., "Metformin in Cancer Therapy: a New Perspective for an Old Antidiabetic Drug?", Mol Cancer Ther, 2010, 9(5): 1092-9.
Vander Heiden et al., "Growth Factors Can Influence Cell Growth and Survival Through Effects on Glucose Metabolism," Mol Cell Biol, 2001, 21(17): 5899-912.

(Continued)

*Primary Examiner* — Shaojia Anna Jiang
*Assistant Examiner* — Dale R Miller
(74) *Attorney, Agent, or Firm* — Andrus Intellectual Property Law, LLP

(57) ABSTRACT

Disclosed herein are methods of treating, diagnosing, and prognosing GLUT-dependent cancers and OXPHOS-dependent cancers. In some embodiments, the methods comprise administering to a patient in need thereof a GLUT inhibitor and/or an OXPHOS inhibitor. The inhibitors may be administered before, concurrently, or after one another. Suitable GLUT-dependent cancers may include a GLUT4-dependent cancer, a GLUT8-dependent cancer, and a GLUT11-dependent cancer. Suitable GLUT inhibitors may include a GLUT4 inhibitor, a GLUT8 inhibitor, and a GLUT11 inhibitor. Suitable OXPHOS-dependent cancers may include mitochondrial OXPHOS-dependent cancers, including cancers that have developed resistance to treatment with a GLUT-inhibitor.

13 Claims, 25 Drawing Sheets

(56) References Cited

OTHER PUBLICATIONS

Was et al., "Effects of the HIV Protease Inhibitor Ritonavir on GLUT4 Knock-Out Mice," J Biol Chem, 2010, 285(47): 36395-400.

Wuilleme-Toumi et al., "Mcl-1 is Overexpressed in Multiple Myeloma and Associated with Relapse and Shorter Survival," Leukemia, 2005, 19(7): 1248-52.

Xu, et al., "Inhibition of Glycolysis in Cancer Cells: A Novel Strategy to Overcome Drug Resistance Associated with Mitochondrial Respiratory Defect and Hypoxia," Cancer Res, 2005, 65(2): 613-21.

Bartel et al., "F18-Fluorodeoxyglocuse Positron Emission Tomography in the Context of Other Imaging Techniques and Prognostic Factors in Multiple Myeloma," Blood, 2009, 114: 2068-2076.

Castellani et al., "The Prognostic Value of F-18 Fluorodeoxyglocuse Bone Marrow Uptake in Patients with Recent Diagnosis of Multiple Myeloma," Clinical Nuclear Medicine, 2010, 35(1): 1-5.

Gatenby et al., "Why Do Cancers Have High Aerobic Glycolysis?," Nature Reviews, 2004, 4: 891-899.

Lai et al., "Antidiabetes Drugs Correlate with Decreased Risk of Lung Cancer: A Population-Based Observation in Taiwan," Clinical Lung Cancer, 2012, 13(2): 143-148.

MacKenzie et al., "A Phase I Study of Temsirolimus and Metformin in Advanced Solid Tumours," Invest New Drugs, 2012, 30: 647-652.

Richardson et al., "New Treatments for Multiple Myeloma," Oncology, 2005, 19(14): 1781-1795.

Rodriguez-Enriquez et al., "Kinetics of Transport and Phosphorylation of Glucose in Cancer Cells," Journal of Cellular Physiology, 2009, 221: 552-559.

Warburg, "On the Origin of Cancer Cells," Science, 1956, 123(3191): 309-314.

Zamagni et al., Prognostic Relevance of 18-F FDG PET/CT in Newly Diagnosed Multiple Myeloma Patients Treated with Up-Front Autologous Transplantation, Blood, 2011, 118: 5989-5995.

\* cited by examiner

DLBCL and Mantle cancer cell lines.

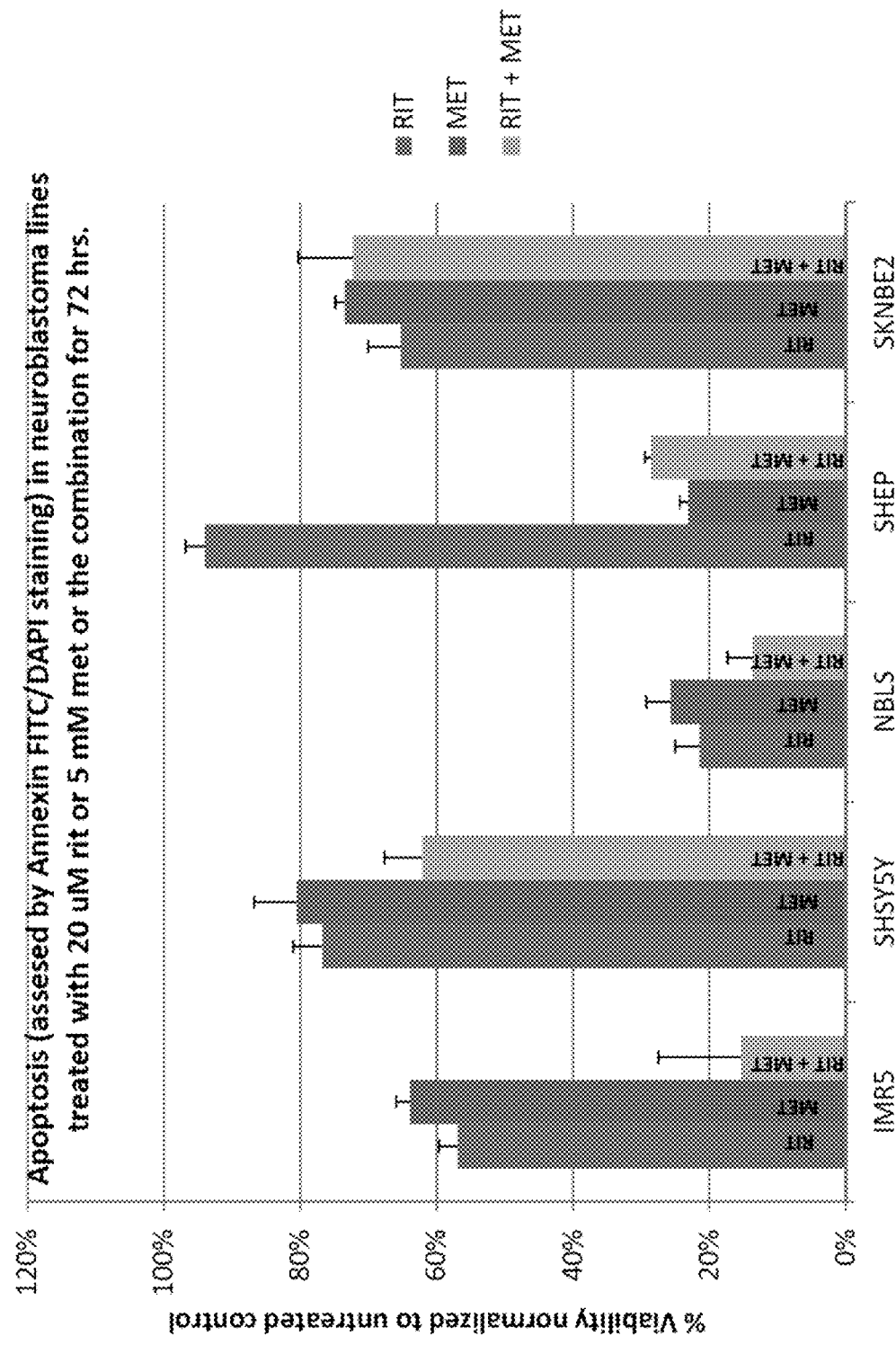

METHODS OF TREATING CANCER WITH GLUT INHIBITORS AND OXIDATIVE PHOSPHORYLATION INHIBITORS

CROSS-REFERENCE TO RELATED PATENT APPLICATIONS

The present application claims the benefit of priority under 35 U.S.C. §119(e) to U.S. Provisional Patent Application No. 61/723,079, filed on Nov. 6, 2012, the content of which is incorporated by reference in its entirety.

BACKGROUND

Multiple Myeloma (MM) is an incurable plasma cell malignancy accounting for 11,000 deaths annually in the US and 20% of deaths from all hematological malignancies. Therefore, there is a great need for the development of therapeutics with efficacy in treating aggressive chemo-resistant MM. Myeloma is characterized by a high degree of genetic heterogeneity, and targeting tumor cell metabolism may provide a unifying therapeutic strategy to target the broader spectrum of cell types. Elevated glucose consumption in MM forms the basis for the diagnostic imaging modality $^{18}$fluoro-deoxyglucose positron emission tomography (FOG-PET) in addition to being a prognostic indicator. Glucose metabolism has not however been directly targeted for therapy in any cancer. We recently identified glucose transporters (GLUTs), including GLUT4, as playing a major role in facilitating glucose transport and maintenance of viability in MM. We further demonstrated the utility of repurposing human immunodeficiency virus (HIV) protease inhibitors with off-target inhibitory effects on GLUT4 to target GLUT4 in MM. GLUT4 inhibition leads to growth inhibition and/or apoptosis.

We have recently determined that MM cells that have developed resistance to GLUT4 inhibition/ritonavir utilize mitochondrial metabolism coupled to oxidative phosphorylation (i.e., mitochondrial OXPHOS) in order to remain viable. Metformin HCl, sold under the trademark GLUCOPHAGE®, is a mitochondrial complex 1 inhibitor that can be used to target mitochondrial OXPHOS. GLUT family members exhibit restricted expression profiled in normal tissues and have a rate-limiting role in the glycolytic pathway, suggesting that GLUT inhibition combined with mitochondrial OXPHOS inhibition may provide a cancer therapy having a high therapeutic index. Here, we demonstrate that targeting GLUT4-driven glycolysis with ritonavir and any ensuing compensatory mitochondrial metabolism with metformin elicits potent lethality across a spectrum of cancers. Hence, we propose that HIV protease inhibitors with off-target inhibitory effects on GLUT4 may be repurposed and administered in combination with metformin to treat a spectrum of cancers capable of utilizing glycolytic or mitochondrial metabolism. Ritonavir has also been shown to inhibit other GLUTs. These additional GLUT inhibitory activities may be beneficial to target GLUT-driven malignancies in combination with metformin to target any compensatory mitochondrial metabolism.

SUMMARY

Disclosed herein are methods of treating, diagnosing, and prognosing GLUT-dependent cancers and OXPHOS-dependent cancers. In some embodiments, the methods may comprise administering to a patient in need thereof a GLUT inhibitor and/or an OXPHOS inhibitor. The inhibitors may be administered before, concurrently, or after one another. Suitable GLUT-dependent cancers may include a GLUT4-dependent cancer, a GLUT8-dependent cancer, and a GLUT11-dependent cancer. Suitable GLUT inhibitors may include a GLUT4 inhibitor, a GLUT8 inhibitor, and a GLUT11 inhibitor. Suitable OXPHOS-dependent cancers may include mitochondrial OXPHOS-dependent cancers, including cancers that have developed resistance to treatment with a GLUT-inhibitor and are amenable to treatment with OXPHOS inhibitors.

In some embodiments of the disclosed methods, the GLUT-dependent cancer is a GLUT4-dependent cancer, which may include multiple myeloma, chronic lymphocyte leukemia (CLL), large B cell lymphoma, breast cancer, ovarian cancer, melanoma, and neuroblastoma. In some embodiments, the GLUT inhibitor is a GLUT4 inhibitor, which may include ritonavir or indinavir. In other embodiments of the disclosed methods, the GLUT-dependent cancer is a GLUT8-dependent cancer, which may include multiple myeloma, chronic lymphocyte leukemia (CLL), large B cell lymphoma, breast cancer, ovarian cancer, melanoma, and neuroblastoma. In further embodiments of the disclosed methods, the GLUT-dependent cancer is a GLUT11-dependent cancer, which may include multiple myeloma, chronic lymphocyte leukemia (CLL), large B cell lymphoma, breast cancer, ovarian cancer, melanoma, and neuroblastoma.

In some embodiments, the OXPHOS-dependent cancer is a cancer that is resistant to treatment with a GLUT inhibitor, such as a mitochondrial OXPHOS-dependent cancer, which may include multiple myeloma, chronic lymphocyte leukemia (CLL), large B cell lymphoma, breast cancer, ovarian cancer, melanoma, and neuroblastoma. Suitable OXPHOS inhibitors may include inhibitors of mitochondrial OXPHOS, which may include biguanide compounds such as metformin, phenformin, buformin, and pharmaceutically acceptable salts thereof.

Optionally, the methods further comprise administering a DNA damaging agent. In some embodiments, the DNA damaging agent is selected from doxorubicin, daunorubicin, epirubicin, idarubicin, valrubicin, and mitoxantrone.

Optionally, the methods further comprise administering a proteasome inhibitor. In some embodiments, the proteasome inhibitor is selected from bortezomib, disulfiram, epigallo-catechin-3-gallate, and salinosporamide A.

In some embodiments of the disclosed methods, the GLUT inhibitor and/or OXPHOS inhibitor is administered after the patient has fasted. For example, a GLUT inhibitor and/or OXPHOS inhibitor may be administered after the patient has fasted for at least 4 hours, at least 6 hours, or at least 12 hours.

Also disclosed herein are methods of diagnosing or prognosing GLUT-dependent and/or OXPHOS-dependent cancers. In some embodiments, the methods may include predicting whether a cancer patient will respond to treatment with a GLUT inhibitor and/or an OXPHOS inhibitor. In some embodiments, the methods comprise detecting a GLUT in cancer cells from the patient, wherein an elevated level of the GLUT and/or a mislocalization of the GLUT indicates that the patient will respond to treatment with the GLUT inhibitor and/or OXPHOS inhibitor.

In some embodiments of the methods of predicting whether a cancer patient will respond to treatment with a GLUT inhibitor and/or OXPHOS inhibitor, the methods comprise detecting GLUT4 in cancer cells from the patient, which may include detecting GLUT4 mislocalization in the cancer cells such as detecting mislocalization of GLUT4 to the plasma membrane. Detecting mislocalization of GLUT4 may indicate that the patient will respond to treatment with a GLUT4 inhibitor. In some embodiments, detecting mislocalization comprises detecting increased localization of GLUT4 to the plasma membrane of the cancer cells.

In other embodiments of the methods of predicting whether a cancer patient will respond to treatment with a GLUT inhibitor, the methods comprise detecting GLUT8 in cancer cells from the patient. An elevated level of GLUT8 may indicate that the patient will respond to treatment with a GLUT8 inhibitor.

In further embodiments of the methods of predicting whether a cancer patient will respond to treatment with a GLUT inhibitor, the methods comprise detecting GLUT11 in cancer cells from the patient. An elevated level of GLUT11 may indicate that the patient will respond to treatment with a GLUT11 inhibitor.

In some embodiments of the methods of predicting whether a cancer patient will respond to treatment with a GLUT inhibitor, the cancer cells are cancer cells of blood. Suitable cancer cells for the methods of predicting whether a cancer patient will respond to treatment with a GLUT inhibitor include multiple myeloma cells, chronic lymphocyte leukemia (CLL) cells, and large B cell lymphoma cells, breast cancer cells, ovarian cancer cells, melanoma cells, and neuroblastoma cells.

In some embodiments, the methods including predicting that a cancer in a patient is resistant to treatment with a GLUT inhibitor. Subsequently, the patient then may be administered an OXPHOS inhibitor.

The disclosed methods of predicting whether a cancer patient will respond to treatment with a GLUT inhibitor may include a step of requesting a test providing results of an analysis to detect a GLUT in cancer cells from a biological sample of a patient. In some embodiments, the methods further may include administering a GLUT inhibitor and/or an OXPHOS inhibitor if an elevated level of the GLUT in the cancer cells is detected or if the GLUT is detected as being mislocalized in the cancer cells.

DETAILED DESCRIPTION

Definitions

Figure 1A:
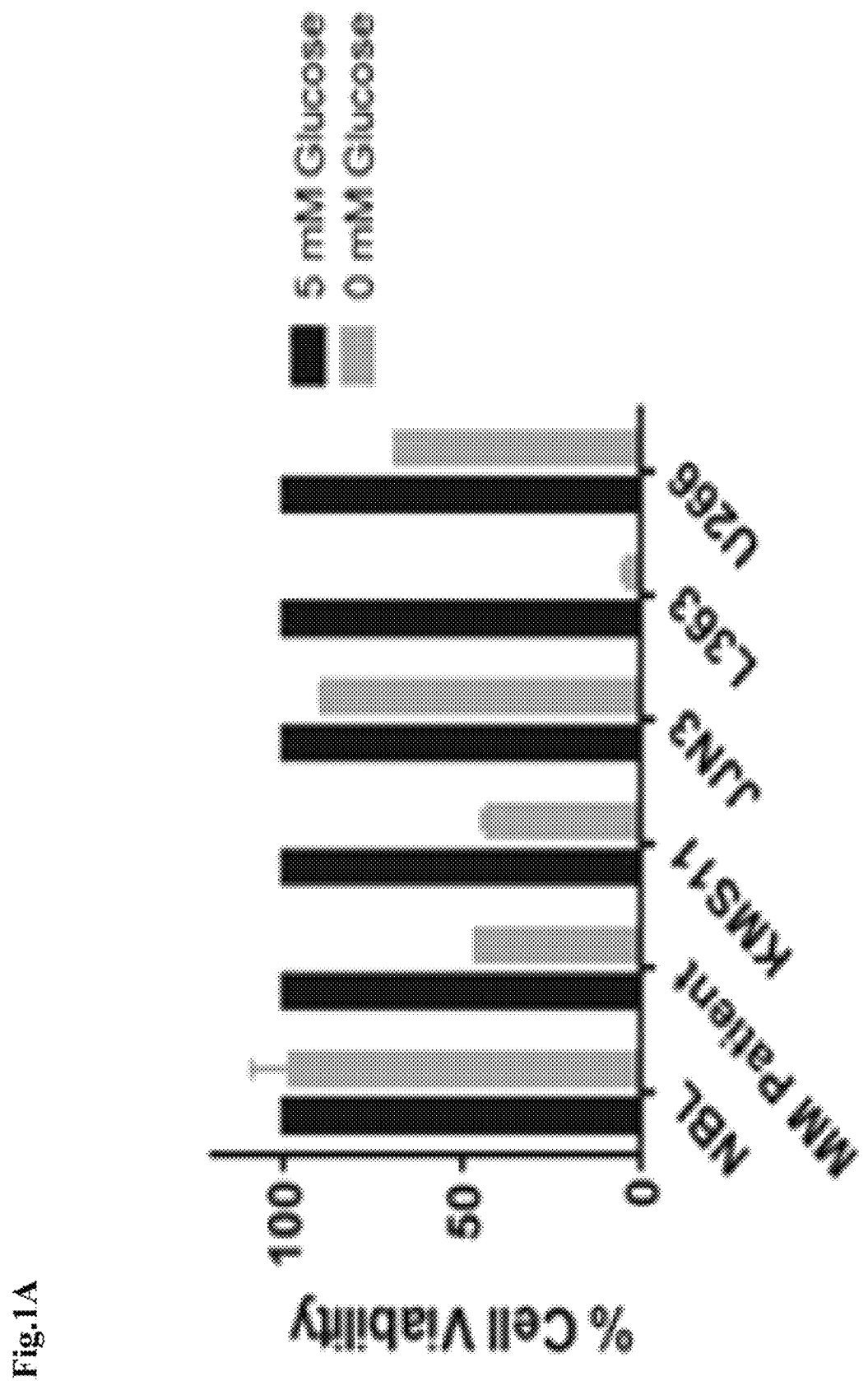
FIG. 1. Glucose metabolism sustains myeloma cell proliferation, viability and promotes chemoresistance: (A) Primary myeloma cells, normal B lymphocytes (NBL) and four MM cell lines were cultured in medium containing 0 or 5 mM glucose for 48 (NBL, MM cell lines) or 72 (MM Patient) hours. Cell viability was determined by flow cytometric analysis of AnnexinV/DAPI staining and normalized to 5 mM samples. Data are means±SEM (n=2 for MM cell lines and NBL. n=1 for MM Patient sample). (B) MM cell lines were cultured in various glucose concentrations for 72 hours. Viable cell quantities were determined by MTS assay (represented by absorbance at 490 nm) and normalized to 5 mM samples. U266 cells (C) and normal PBMC (D) were cultured in 11 mM or 0.5 mM glucose-containing medium for 48 hours in the presence of the indicated concentrations of doxorubicin. Cell death was determined by OAPI staining. GLUT4 knockdown was observed to reduce glucose uptake and lactate production and to induce apoptosis and/or growth arrest in myeloma while GLUT4 knockdown was observed to be less effective: Cells were transduced with control, non-targeted shRNA or GLUT4-targeted shRNA and incubated 3 (L363) or 4 (JJN3, KMS11) days before protein extraction and analysis of GLUT4 protein expression was performed. Representative blot is shown (E). (F) Cells from part E were cultured in 5 mM glucose-containing medium for 5 hours. Glucose consumption rates and lactate production rates were determined and normalized to control shRNA-expressing cells. (G-I) Cells from part (E) were analyzed for viability and proliferation. (J) JJN3 cells transduced with control or GLUT1-targeted shRNA and analyzed for viability and proliferation. Viable cell densities are expressed as fold change relative to the day 0 reading of control shRNA-expressing cells. Cells from parts G-J were evaluated for viability via trypan blue exclusion. Values are normalized to control shRNA-expressing cells. Parts A-J except E are means±SEM, n≥3 and *P<0.05P<0.01*P<0.005

The subject matter disclosed herein is described using several definitions, as set forth below and throughout the application.

Unless otherwise noted, the terms used herein are to be understood according to conventional usage by those of ordinary skill in the relevant art. In addition to the definitions of terms provided below, it is to be understood that as used in the specification, embodiments, and in the claims, "a", "an", and "the" can mean one or more, depending upon the context in which it is used.

As used herein, "about," "approximately," "substantially." and "significantly" will be understood by persons of ordinary skill in the art and will vary to some extent on the context in which they are used. If there are uses of the term which are not clear to persons of ordinary skill in the art given the context in which it is used, "about" or "approximately" will mean up to plus or minus 10% of the particular term and "substantially" and "significantly" will mean more than plus or minus 10, of the particular term.

As used herein, the terms "include" and "including" have the same meaning as the terms "comprise" and "comprising."

As used herein, the terms "patient" and "subject" may be used interchangeably and refer to one who receives medical care, attention or treatment. As used herein, the term is meant to encompass a person diagnosed with a disease such as cancer or at risk for developing cancer (e.g., a person who may be symptomatic for a cancer but who has not yet been diagnosed). A "patient in need thereof" may include a patient having, suspected of having, or at risk for developing a cell proliferative disorder or disease such as cancer, including multiple myeloma, chronic lymphocyte leukemia (CLL), large B cell lymphoma, breast cancer, ovarian cancer, melanoma, and neuroblastoma.

As used herein, the term "treatment," "treating," or "treat" refers to care by procedures or application that are intended to relieve illness or injury. Although it is preferred that treating a condition or disease such as multiple myeloma, chronic lymphocyte leukemia (CLL), and large B cell lymphoma will result in an improvement of the condition, the term treating as used herein does not indicate, imply, or require that the procedures or applications are at all successful in ameliorating symptoms associated with any particular condition. Treating a patient may result in adverse side effects or even a worsening of the condition which the treatment was intended to improve.

Treating may include treating a patient having, suspected of having, or at risk for developing a cell proliferative disorder or disease such as cancer, including multiple myeloma, chronic lymphocyte leukemia (CLL), large B cell lymphoma, breast cancer, ovarian cancer, melanoma, and neuroblastoma.

As used herein the term "effective amount" refers to the amount or dose of the agent, upon single or multiple dose administration to the subject, which provides the desired effect in the subject under diagnosis or treatment. The disclosed methods may include administering an effective amount of the disclosed agents (e.g., as present in a pharmaceutical composition) for treating a cancer in the patient, whereby the effective amount slows the growth of, or reduces the size or extent of, the cancer.

An effective amount can be readily determined by the attending diagnostician, as one skilled in the art, by the use of known techniques and by observing results obtained under analogous circumstances. In determining the effective amount or dose of agent administered, a number of factors can be considered by the attending diagnostician, such as: the species of the patient; its size, age, and general health; the degree of involvement or the severity of the cancer; the response of the individual patient; the particular agent administered; the mode of administration: the bioavailability characteristics of the preparation administered; the dose regimen selected; the use of concomitant medication; and other relevant circumstances.

As used herein, the term "GLUT-dependent cancer" refers to a cancer in which there is an elevated level of at least one GLUT protein, mRNA, or pre-mRNA in at least some of the cancer cells, and/or in which at least one GLUT protein is mislocalized in at least some of the cancer cells. In some embodiments, there is an elevated level of at least one GLUT protein, mRNA, or pre-mRNA in at least 30%, at least 50%, or at least 75% of the cancer cells in a sample of cancer cells from the patient. In some embodiments, at least one GLUT protein is mislocalized in at least 30%, at least 50%, or at least 75% of the cancer cells in a sample of cancer cells from the patient. GLUT-dependent cancers include, but are not limited to, GLUT4-dependent cancers, GLUT8-dependent cancers, and GLUT11-dependent cancers. A particular GLUT-dependent cancer may be classified as more than one of a GLUT4-dependent cancer, a GLUT8-dependent cancer, a GLUT11-dependent cancer, etc. Multiple myeloma is a nonlimiting exemplary GLUT4-dependent cancer. Multiple myeloma is also a nonlimiting exemplary GLUT8-dependent cancer, and a nonlimiting exemplary GLUT11-dependent cancer.

As used herein, the term "GLUT inhibitor" refers to an agent that inhibits the activity of a GLUT protein, for example by direct inhibition of the protein, or by inhibition of expression of the protein. GLUT inhibitors include, but are not limited to, GLUT4 inhibitors, GLUT8 inhibitors, and GLUT11 inhibitors. Nonlimiting exemplary GLUT4 inhibitors include ritonavir, indinavir, and pharmaceutically acceptable salts thereof.

GLUT inhibitors may include analogs or derivatives of ritonavir, which may include "similar compounds as defined in the National Center for Biotechnology Information's PubChem database, such as compounds identified by the compound identification numbers (CID's): CID: 392622; CID: 16760215; CID: 10395099; CID: 9853294; CID: 60954; CID: 5076; CID: 44371188; CID: 44371171; CID: 44371165; CID: 44371081; CID: 44371069; CID:

CID: 44371023; CID: 44371021; CID: 44371020; CID: 44371019; CID: 44371018; CID: 44370991; CID: 22878492; CID: 22868003; CID: 22863118; CID: 22863027; CID: 22863019; CID: 22862950; CID: 22862923; CID: 19432988; CID: 18759200; CID: 18759116; CID: 18759083; CID: 18759081; CID: 18759065; CID: 18759050; CID: 18759039; CID: 18758899; CID: 18758893; CID: 18758866; CID: 18758863; CID: 18758854; CID: 18624597; CID: 515847; CID: 515824; CID: 515823; CID: 515818; CID: 515817; CID: 515815; CID: 482962; CID: 482960; CID: 482957; CID: 482956; CID: 482948; CID: 482947; CID: 482944; CID: 482943; CID: 49823250; CID: 44371241; CID: 44371229; CID: 44371228; CID: 44371227; CID: 44371170; CID: 44371169; CID: 44371108; CID: 44370961; CID: 44370960; CID: 44370959; CID: 44370896; CID: 44370895; CID: 44370881; CID: 44334979; CID: 22878493; CID: 22867769; CID: 22865244; CID: 22863127; CID: 22863125; CID: 22863035; CID: 22863031; CID: 22863015; CID: 22863014; CID: 22863010; CID: 22862997; CID: 22862993; CID: 22862986; CID: 22862979; CID: 22862969; CID: 22862946; CID: 22862939; CID: 22862927; CID: 22862919; CID: 22862904; CID: 22862857; CID: 22862838; CID: 22862827; CID: 22862817; CID: 18759212; CID: 18759181; and CID: 18759178; which entries are incorporated herein by reference in their entireties.

GLUT inhibitors may include analogs or derivatives of indinavir, which may include "similar compounds" as defined in the National Center for Biotechnology Information's PubChem database, such as compounds identified by the compound identification numbers (CID's): CID: 5362440; CID: 46930980; CID: 23351650; CID: 23351649; CID: 11399365; CID: 9830402; CID: 9830401; CID: 3033831; CID: 60944; CID: 3706; CID: 51346630; CID: 23232405; CID: 44629557; CID: 24848178; CID: 5496641; CID: 5495865; CID: 5495864; CID: 5493607; CID: 5484730; CID: 3400922; CID: 508523; CID: 508522; CID: 496986; CID: 446635; CID: 104877; CID: 44366310; CID: 44343215; CID: 20870851; CID: 18477694; CID: 16639401; CID: 16639395; CID: 5479510; CID: 455962; CID: 44366356; CID: 44366297; CID: 44342144; CID: 23375344; CID: 20979070; CID: 18730500; CID: 10974220; CID: 10941221; CID: 10908345; CID: 9853161; CID: 5496583; CID: 5481985; CID: 489318; CID: 480986; CID: 446133; CID: 49757450; CID: 46930979; CID: 44628479; CID: 44366619; CID: 44366414; CID: 44366309; CID: 44342037; CID: 44326584; CID: 23377516; CID: 23375501; CID: 20846145; CID: 11954281; CID: 9874011; CID: 5481045; CID: 5481043; CID: 5462355; CID: 469114; CID: 469111; CID: 394079; CID: 60958; CID: 44563986 CID: 44563984; CID: 44367246; CID: 44366592; CID: 44366576; CID: 25015662; CID: 24970688; CID: 24892955; CID: 24892954; CID: 23351700; CID: 23315005; CID: 23305628; CID: 22489378; CID: 21576401; CID: 21147539; CID: 20842172; CID: 18002348; CID: 9988227; CID: 9940047; CID: 9832401; CID: 6475670; CID: 5481046; CID: 5481044; CID: 5464652; CID: 493833; CID: 479179; CID: 479178; CID: 479168; CID: 469115; CID: 469112; CID: 44366295; and CID: 44342145; which entries are incorporated herein by reference in their entireties.

As used herein, the term "OXPHOS inhibitor" refers to an agent that inhibits oxidative phosphorylation, for example, oxidative phosphorylation in the mitochondria, either by direct inhibition of proteins involved in oxidative phosphorylation, or by inhibition of expression of the proteins involved in oxidative phosphorylation. OXPHOS inhibitors include, but are not limited to, compounds within the biguanide class of drugs, such as metformin, phenformin, buformin, and pharmaceutically acceptable salts thereof. OXPHOS inhibitors may include analogs or derivatives of metformin, which may include "similar compounds" as defined in the National Center for Biotechnology Information's PubChem database, such as compounds identified by the compound identification numbers (CID's): CID: 4091; CID: 45039708; CID: 60003225; CID: 10313238; CID: 43061781; CID: 3043660; CID: 53630812; CID: 45039707; CID: 44573417; CID: 211771181; CID: 11310327; CID: 22230); CID: 14219; CID: 53307485; CID: 21027224; CID: 55281088; CID: 53307484; CID: 29530186; CID: 23615830; CID: 21122269; CID: 21023741; CID: 20314408; CID: 16235945; CID: 15949929; CID: 121135; CID: 58635196; CID: 18921325; CID: 141619; and CID: 15603; which entries are incorporated herein by reference in their entireties.

As used herein, the term "DNA damaging agent" refers to a therapeutic agent that damages replicating DNA. In some embodiments, a DNA damaging agent damages cancer cell DNA. In some embodiments, a DNA damaging agent is used to treat cancer, for example, in combination with a GLUT inhibitor, as described herein. Nonlimiting exemplary DNA damaging agents include, but are not limited to, doxorubicin, daunorubicin, epirubicin, idarubicin, valrubicin, and mitoxantrone.

As used herein, the term "fasted" indicates that a patient has not taken in, by mouth, feeding tube, intravenously, or other route, a substance containing glucose for a certain length of time. When a patient has only eliminated glucose for a certain length of time, the fast may be referred to herein as a "glucose fast." In some embodiments, a fasting patient has not taken in a substance containing calories (referred to herein as a "caloric fast"). In some embodiments, a fasting patient has not taken in any substances except water (referred to herein as a "complete fast"). In some embodiments, a fasting patient has not taken in any substances, including water (referred to herein as a "complete fast without water").

The term "proteasome inhibitor" as used herein refers to an agent that blocks the action of proteasomes, which are cellular complexes that break down proteins. In some embodiments, a proteasome inhibitor is used to treat cancer, for example, in combination with a GLUT inhibitor, as described herein. Suitable proteasome inhibitors for use in the methods disclosed herein may include but are not limited to peptide boronic acid compounds. NPI-0052 (salinosporamide A analogs), 2-pyrrolidone compounds, epigallocatechin 3-gallate (EGCG) analogs (in particular those analogs that are specific for proteasome inhibition), PR-171, epoxomycin analogs, peptide analogs, tetrapeptide derivatives, tyropeptide A analogs, and combinations thereof. In some embodiments, the proteasome inhibitor inhibits one or more enzymatic activities of a proteasome selected from β1 subunit activity (chymotryptic-like activity). β2 subunit activity (tryptic-like activity), and β35 subunit activity (post-glutamyl peptidyl hydrolytic-like activity). One suitable proteasome inhibitor is bortezomib (BZ) or a pharmaceutically acceptable salt thereof, which for example, may be administered to a patient at a dosage of about of about 0.7 mg/m$^2$ to about 1.9 mg/m$^2$. Preferably, the proteasome inhibitor selectively inhibits proteasome activity. Nonlimiting exemplary proteasome inhibitors include bortezomib, disulfiram, epigallocatechin-3-gallate, and salinosporamide A.

The term "mislocalization" as used herein refers to a difference in the intracellular localization of a protein in a cancer cell relative to the localization of the protein in a control cell of similar type. For example, a protein is considered mislocalized if it is located throughout the cytoplasm in a control cell, but is present more predominantly at the cell membrane in a cancer cell (compared to the control cell), whether or not the protein is also located throughout the cytoplasm in the cancer cell. Nonlimiting exemplary control cells for a multiple myeloma are normal B lymphocytes.

A biological molecule is considered to be present at an "elevated level," as used herein, when the biological molecule is present as levels that are at least 20% greater in a cancer cell than in a control cell of similar type. Biological molecules include, but are not limited to, proteins, pre-mRNA, and mRNA.

In some embodiments of the disclosed methods of treating cancer, the methods include administering a GLUT inhibitor. In some such embodiments of the methods of treating cancer, the cancer is a GLUT-dependent cancer. Non-limiting exemplary GLUT-dependent cancers include multiple myeloma, chronic lymphocyte leukemia (CLL), large B cell lymphoma, breast cancer, ovarian cancer, melanoma, and neuroblastoma. The GLUT-dependent cancer may be a GLUT4-dependent, GLUT8-dependent, and/or a GLUT11-dependent cancer.

In some embodiments of the disclosed methods of treating cancer, the cancer is treated with a GLUT4 inhibitor. Suitable cancers for treatment in these include multiple myeloma, chronic lymphocyte leukemia (CLL), large B cell lymphoma, breast cancer, ovarian cancer, melanoma, and neuroblastoma. Non-limiting exemplary GLUT4 inhibitors include the protease inhibitors ritonavir, indinavir, analogs, derivatives, and pharmaceutically acceptable salts thereof. In some embodiments, GLUT4 is mislocalized in multiple myeloma cells, chronic lymphocyte leukemia (CLL) cells, and large B cell lymphoma cells. Typically, GLUT4 is located in the cytoplasm, and localizes to the plasma membrane in an insulin-dependent manner. In multiple myeloma cells, in some embodiments, GLUT4 accumulates at the plasma membrane in the absence of insulin. Accordingly, in some embodiments, a GLUT4 inhibitor can be used to target multiple myeloma cells specifically by administering the GLUT4 inhibitor under fasting conditions, such that GLUT4 is not plasma membrane-localized in normal cells in which GLUT4 localization is insulin-responsive. In various embodiments, the fasting conditions are glucose fasting conditions, caloric fasting conditions, complete fasting conditions, or complete fasting conditions without water. In some embodiments, the patient has fasted for at least 2, at least 4, at least 6, at least 8, or at least 12 hours before administration of the GLUT4 inhibitor.

In some embodiments of the disclosed methods of treating cancer, the cancer is treated with a GLUT8 inhibitor. Suitable cancers for treatment in these include multiple myeloma, chronic lymphocyte leukemia (CLL), large B cell lymphoma, breast cancer, ovarian cancer, melanoma, and neuroblastoma. In some embodiments, GLUT8 is present at higher levels, at the protein and/or mRNA level, in the cancer cells. Thus, in some embodiments, a GLUT8-dependent cancer may be more sensitive to a GLUT8 inhibitor than normal cells.

In some embodiments of the disclosed methods of treating cancer, the cancer is treated with a GLUT11 inhibitor. Suitable cancers for treatment in these include multiple myeloma, chronic lymphocyte leukemia (CLL), large B cell lymphoma, breast cancer, ovarian cancer, melanoma, and neuroblastoma. In some embodiments, GLUT11 is present at higher levels, at the protein and/or mRNA level, in the cancer cells. Thus, in some embodiments, a GLUT11-dependent cancer may be more sensitive to a GLUT11 inhibitor than normal cells.

In some embodiments of the disclosed methods of treating cancer, a GLUT-dependent cancer is treated with a combination therapy comprising a GLUT inhibitor and one or more additional therapeutic molecules. In some embodiments, a GLUT-dependent cancer is treated with the combination of a GLUT inhibitor and a DNA damaging agent. In some such embodiments, the cancer is a GLUT4-dependent cancer and the GLUT inhibitor is a GLUT4 inhibitor. Thus, in some embodiments, a GLUT4-dependent cancer is treated with the combination of a GLUT4 inhibitor and a DNA damaging agent. Non-limiting exemplary DNA damaging agents include doxorubicin, daunorubicin, epirubicin, idarubicin, valrubicin, and mitoxantrone. In some embodiments, a GLUT4-dependent cancer is treated with the combination of a GLUT4 inhibitor and doxorubicin. In some embodiments, a GLUT4-dependent cancer is treated with the combination of ritonavir and/or indinavir, and doxorubicin. In some embodiments, multiple myeloma, chronic lymphocyte leukemia (CLL), large B cell lymphoma, breast cancer, ovarian cancer, melanoma, or neuroblastoma is treated with a combination of ritonavir and % or indinavir, and doxorubicin.

In some embodiments of the disclosed methods of treating cancer, a GLUT-dependent cancer is treated with the combination of a GLUT inhibitor and a proteasome inhibitor. In some such embodiments, the cancer is a GLUT8-dependent cancer and the GLUT inhibitor is a GLUT8 inhibitor. Non-limiting exemplary proteasome inhibitors include bortezomib, disulfiram, epigallocatechin-3-gallate, and salinosporamide A. In some embodiments, a cancer is treated with the combination of a GLUT8 inhibitor and bortezomib.

In some embodiments of the disclosed methods of diagnosing and/or prognosing cancer, methods of predicting whether a cancer patient will respond to treatment with a GLUT inhibitor are provided. In some such embodiments, the method comprises detecting the level of a GLUT protein, mRNA, and/or pre-mRNA in the cancer cells. The level of a GLUT protein, mRNA, and/or pre-mRNA can be determined by any method. Many such methods are known in the art, and one skilled in the art can select a suitable method for determining the level of a particular protein, mRNA, and/or pre-mRNA in a cell. In some embodiments, the level of the protein, mRNA, and/or pre-mRNA in the cancer cell is compared to the level of the same protein, mRNA, and/or pre-mRNA in a control cell or normal cell. In some embodiments, the level of a GLUT protein, mRNA, and/or pre-mRNA in the cancer cell is compared to the level of a control protein, mRNA, and/or pre-mRNA in the cancer cell, wherein the normal ratio of the level of the control protein, mRNA and/or pre-mRNA to the GLUT protein, mRNA and/or pre-mRNA is known. In some embodiments, if the level of GLUT4, GLUT8, or GLUT11 is elevated in the cancer cell, the cancer is predicted to respond to an inhibitor of GLUT4, GLUT8, or GLUT11.

In some embodiments of the disclosed methods of diagnosing and/or prognosing cancer, the method comprises detecting mislocalization of a GLUT protein in the cancer cells. In some such embodiments, detecting mislocalization of a GLUT protein indicates that a cancer will respond to a GLUT inhibitor. Mislocalization is any difference in the localization of a GLUT protein in a cancer cell relative to a control or normal cell of a similar type. A "similar type" or normal cell includes, for example, the cell type from which the cancer is derived. As a non-limiting example, a normal cell to which a multiple myeloma can be compared is a B lymphocyte. In some embodiments, a difference in the localization of a GLUT protein includes situations in which the GLUT protein is found in all of the same locations as it is found in the normal cell, but at different levels at those locations relative to one another. Thus, for example, if a GLUT protein is localized evenly throughout the cytoplasm in a normal cell, in some embodiments, the GLUT protein is mislocalized in a cancer cell if it is localized evenly throughout the cytoplasm, but is also present at the plasma membrane in higher levels than in the cytoplasm generally, unlike in the normal cell. See, e.g., FIG. 3. As a non-limiting example, mislocalization of GLUT4 to the plasma membrane in multiple myeloma cells indicates that the multiple myeloma will respond to a GLUT4 inhibitor.

The disclosed methods of predicting whether a cancer patient will respond to treatment with a GLUT inhibitor may include a step of requesting a test providing results of an analysis to detect a GLUT in cancer cells from a biological sample of a patient. In some embodiments, the methods may include requesting a test providing results of an analysis to detect a GLUT (e.g., GLUT4, GLUT8, and/or GLUT11) in cancer cells (e.g., multiple myeloma. CLL, or large B cell lymphoma) from a biological sample of the patient (e.g., a blood sample from the patient). Optionally, the methods further may include administering a GLUT inhibitor and an OXPHOS inhibitor if the requested test provides results of an analysis that have detected an elevated level of the GLUT in the cancer cells or if the test provides results of an analysis that detect that the GLUT is mislocalized in the cancer cells.

EXAMPLES

The following examples are illustrative and are not intended to limit the disclosed subject matter.

Example 1

Reference is made to U.S. Published Patent Application No. 2012/0252749, published on Oct. 4, 2012, the content of which is incorporated herein by reference in its entirety.

Example 2

Reference is made to McBrayer et al., "Multiple myeloma exhibits novel dependence on GLUT4, GLUT8, and GLUT11: implications for flucose transporter-directed therapy," Blood. 2012 May 17; 119(20): 4686-4697.

Example 3

Targeting Glycolysis and Compensatory Mitochondrial Metabolism in Multiple Myeloma with FDA Approved Ritonavir and Metformin via Synthetic Lethality
Background
Multiple myeloma (MM) is an incurable plasma cell malignancy accounting for 11,000 deaths annually in the US and 20% of deaths from all hematological malignancies [1,2]. Multiple myeloma is fatal despite use of combinatorial therapeutic regimens and autologous stem cell transplantation due to the development of chemoresistance [1,2]. Therefore there is a great need for the development of therapeutics with efficacy in aggressive, advanced chemoresistant MM. Myeloma is characterized by a high degree of genetic heterogeneity therefore strategies that target the broader spectrum of cell types are desirable. Targeting tumor cell metabolism may provide one such unifying therapeutic strategy. Targeting tumor cell metabolism requires identification of rate-limiting metabolic enzymes regulating key metabolic pathways. In addition, we must identify biochemical pathways contributing to metabolic plasticity that are utilized upon inhibition of specific metabolic enzymes. Glucose metabolism is central to the synthesis of fatty acids, nucleotides, amino acids, ATP and maintenance of redox homeostasis. Therefore, targeting glucose metabolism is therapeutically attractive, the only caveat being the identification of strategies to selectively target tumor cell glucose metabolism. Many tumor cells, including MM, exhibit elevated glucose consumption [3-5] associated with manifestation of the Warburg effect. This elevated glucose uptake in tumors forms the basis for the tumor imaging modality $^{18}$fluoro-deoxyglucose positron emission tomography (FDG-PET) [5-8]. Increased FDG avidity reflects augmented glucose uptake and indicates a poor prognoses in MM [8,9]. While the contributions of increased glucose catabolism to enhanced proliferation, survival and chemoresistance of cancer cells have been well established [10,11], we are yet to successfully target cancer cell-specific glucose metabolism for therapy. Therefore, identification of tumor-specific molecular candidates which drive the glycolytic phenotype could lead to a breakthrough in our ability to treat end-stage myeloma disease as well as other FDG-PET-positive cancers.

Given the restricted expression profiles of glucose transporter (GLUT) family members in normal tissues combined with the rate-determining role played by GLUTs within the glycolytic pathway [12], we hypothesized that these transporters may be ideal therapeutic targets in cancer. In a recently published study, we found that myeloma cells maintain the glycolytic phenotype by maintaining constitutive plasma membrane localization and activation of GLUT4 [13]. GLUT4 inhibition by RNAi suppression or by the use of an HIV protease inhibitor ritonavir that exhibits a selective off-target inhibitory effect on GLUT4 [14] abrogated cell proliferation, chemoresistance and, in a majority of cell lines, induced apoptosis. All of these outcomes correlated with inhibition of MCL-1, which is a pro-survival BCL-2 member that is particularly relevant in MM as MCL-1 expression levels correlate with lower event free survival in MM [15].

Upon discovery of the dependence of MM on GLUT4, we investigated the FDA-approved HIV protease inhibitor ritonavir, which has been demonstrated to selectively inhibit GLUT4 activity in vivo as an off-target effect by non-competitive reversible binding to the exofacial regions of the transporter [14,16,17]. These effects are clinically evidenced from the ensuing insulin resistance and dyslipidemia seen upon chronic administration [18] and validated by studies evaluating ritonavir's impact on glucose tolerance in GLUT4 knockout mice [16]. More recently, ritonavir has also been demonstrated to competitively inhibit the cytoplasmic glucose binding site of GLUT1 and 4 with no selectivity for either transporter [19]. We have determined that treatment of myeloma cell lines and patient samples with physiologically achievable doses of ritonavir exerts glucose transport-specific anti-myeloma effects[13]. Our studies reveal that ritonavir has significant glucose inhibitory and growth inhibitory effects in MM in addition to chemosensitizing resistant MM to a commonly used chemotherapeutic, doxorubicin. The chronic use of ritonavir as part of a combinatorial anti-retroviral treatment regimen for HIV despite its GLUT4-inhibitory effects is proof of principle that humans can tolerate drugs that target GLUT4.

GLUT4-suppressed MM cells exhibit overt toxicity (i.e., sensitivity) or growth inhibition [13]. Similar phenotypes are achieved when MM cells are cultured in glucose-free media or when treated with ritonavir as demonstrated in our recent study [13] and below. Glucose metabolism in the mitochondria regulates cellular viability in part by maintaining mitochondrial membrane potential and integrity. Glucose metabolism via the TCA cycle leads to the generation of reducing equivalents NADH and FADH2 that in turn are oxidized by oxidative phosphorylation to generate a proton gradient and maintain mitochondrial membrane potential. Dissipation of the mitochondrial membrane potential by disruption of the TCA cycle or interference with OXPHOS can lead to the induction of apoptosis. Hence, maintenance of the TCA cycle by glucose metabolism or alternative metabolism is critical for maintenance of cellular viability. We have recently determined that the MM cells resistant to glucose-deprivation/GLUT4 suppression or ritonavir treatment re-program their cellular metabolism to utilize mitochondrial metabolism coupled to OXPHOS (i.e., mitochondrial OXPHOS) to maintain viability.

Metformin is a mitochondrial complex 1 inhibitor that can be used to target mitochondrial OXPHOS. The biguanide metformin is the most commonly prescribed anti-hyperglycemic drug for the treatment of Type II diabetes. Epidemiologic studies have correlated metformin with a reduced risk of cancer in diabetics [20] and more recently in cancer patients [21,22] earning the drug recognition as a possible anti-neoplastic agent for various types of malignancies. Metformin also reduces circulating glucose by increasing insulin sensitivity and lowering glucose production from the liver associated with reduction in insulin levels that also bolsters utility in cancer therapy [23]. We have determined that treating MM cells with both ritonavir and metformin, to target glycolysis and mitochondrial complex 1 activity respectively, induces potent lethality in MM. In addition, the combination of ritonavir and metoformin is cytototoxic in chronic lymphocytic leaukemia cells (CLL), a majority of diffuse large B cell lymphomas (DLBCL), breast, melanoma and neuroblastoma cancer cells. This combinatorial regimen of ritonavir and metformin was not toxic in normal peripheral blood mononuclear cells (PBMC). Our in vivo studies have determined that this selective tumor specific synthetic lethality induced in ritonavir treated MM cells upon metformin treatment is detected at doses that are clinically achievable with both compounds.

Importantly, HIV patients chronically treated with ritonavir who exhibit diabetic symptoms have been treated with metformin indicating this combination treatment is well tolerated in humans 124).

Discussion

Figure 1B:
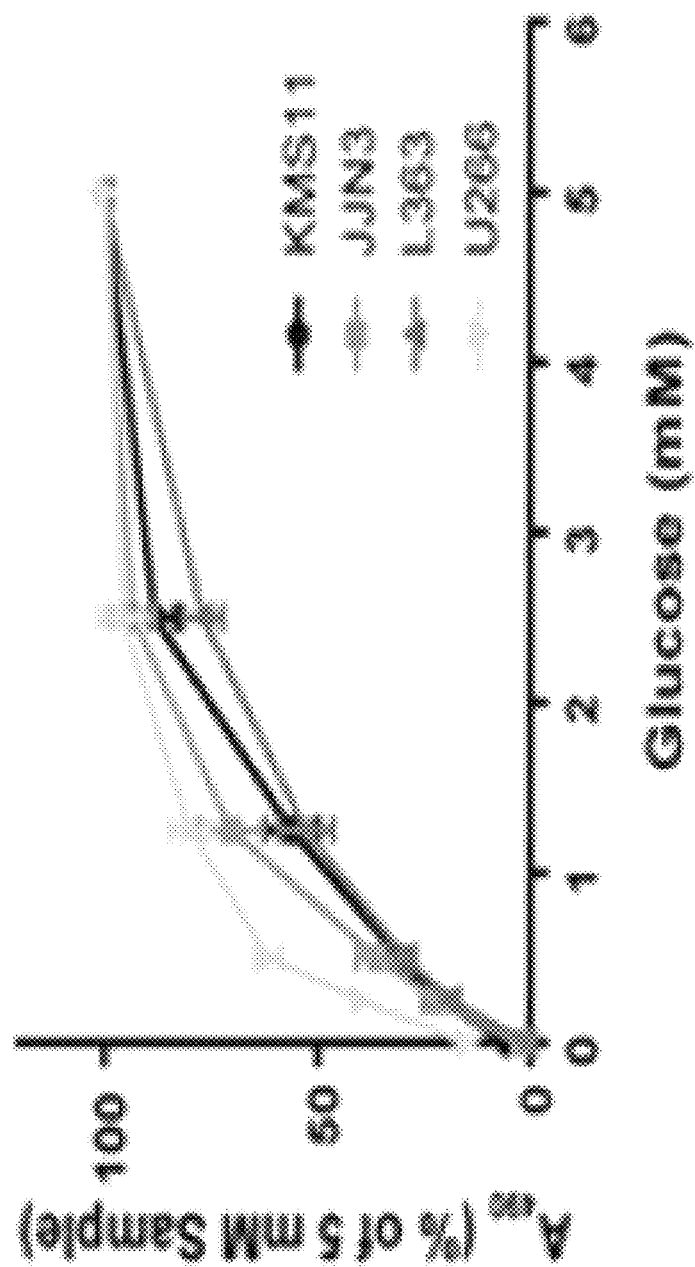
Figure 1C:
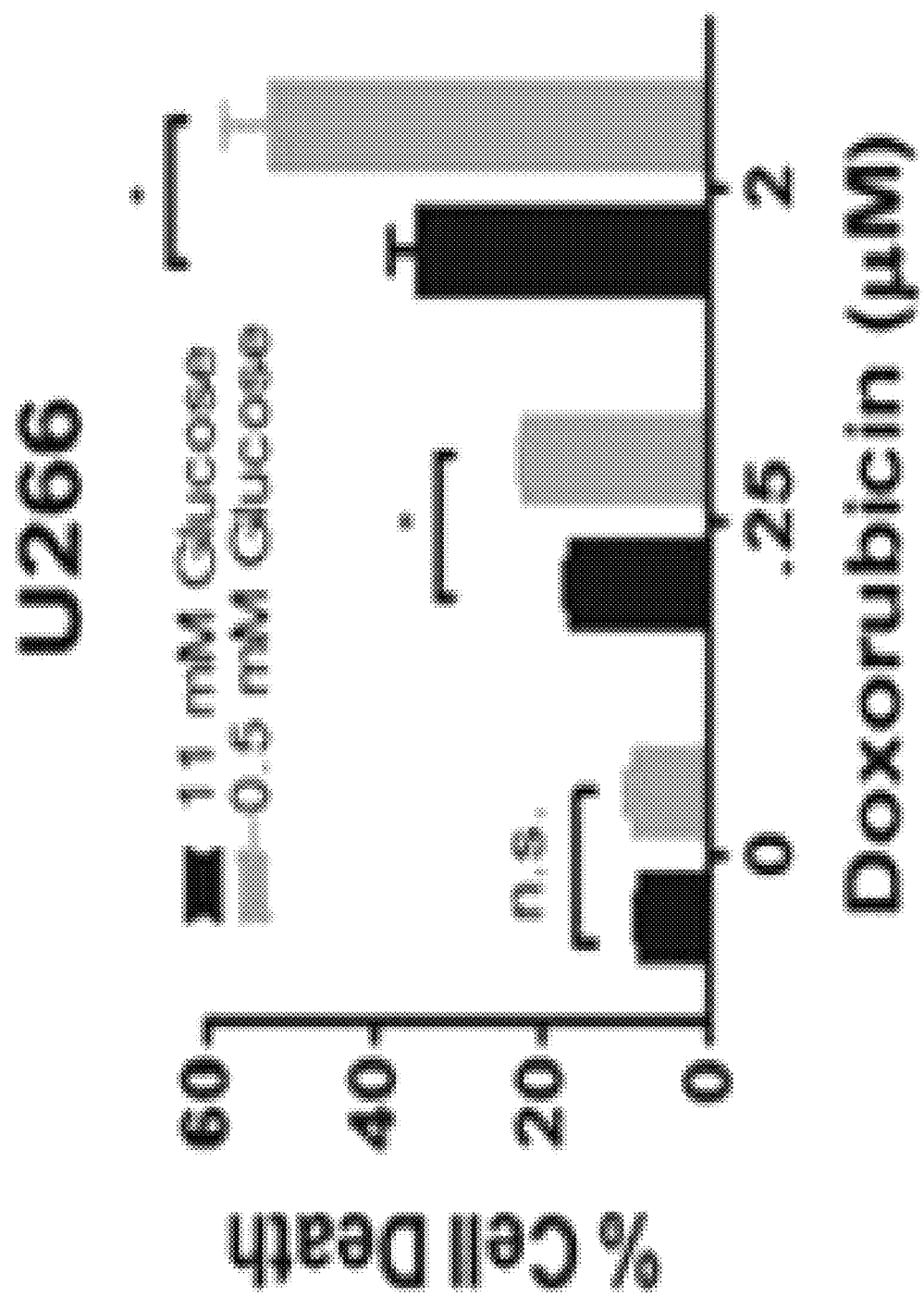
Figure 1D:
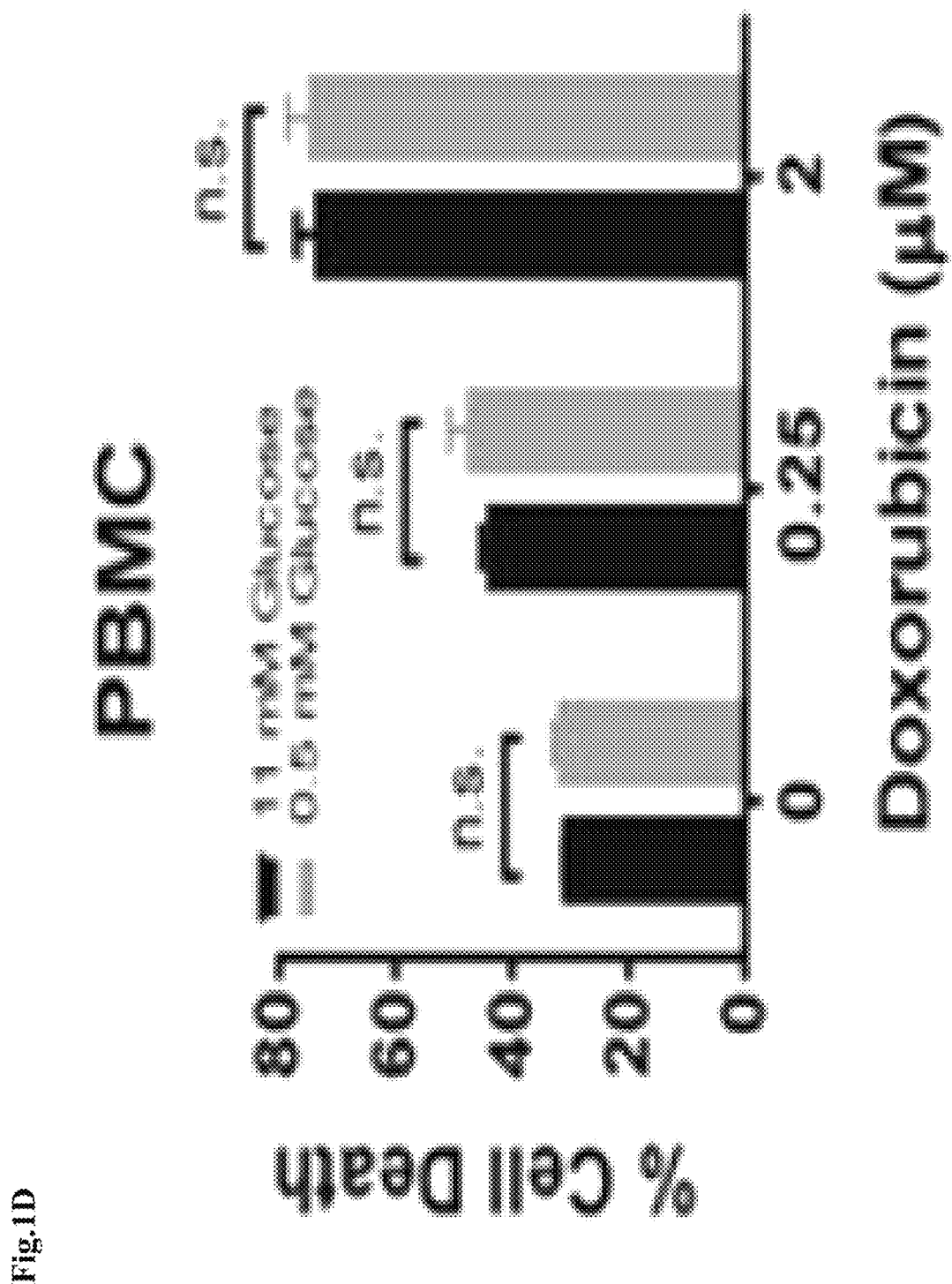
Figure 1E:
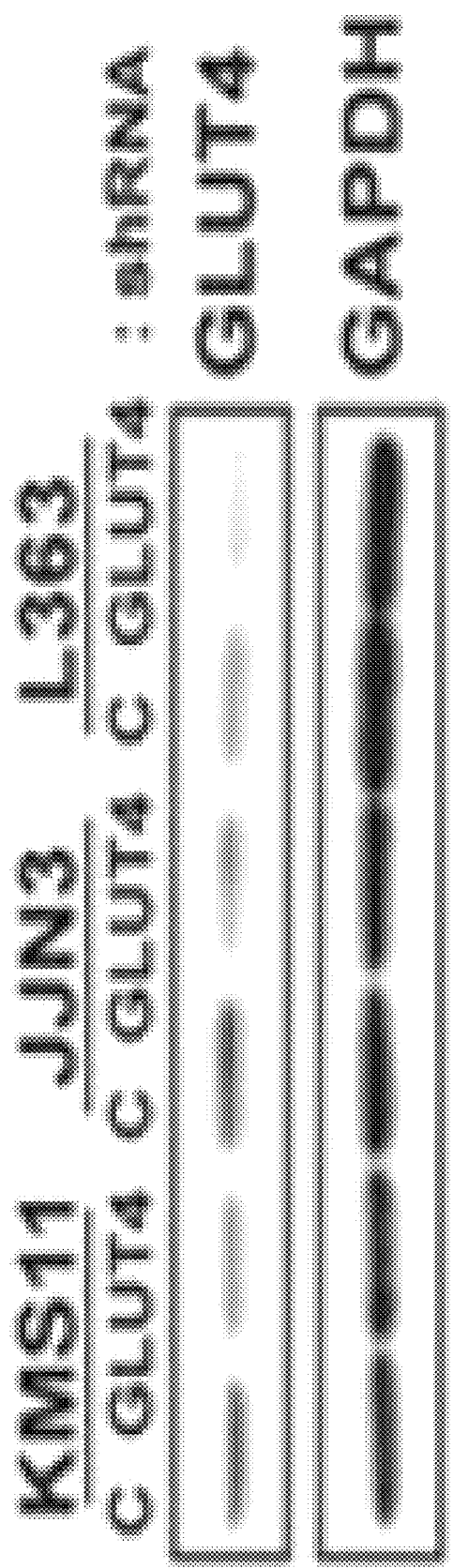
Figure 1F:
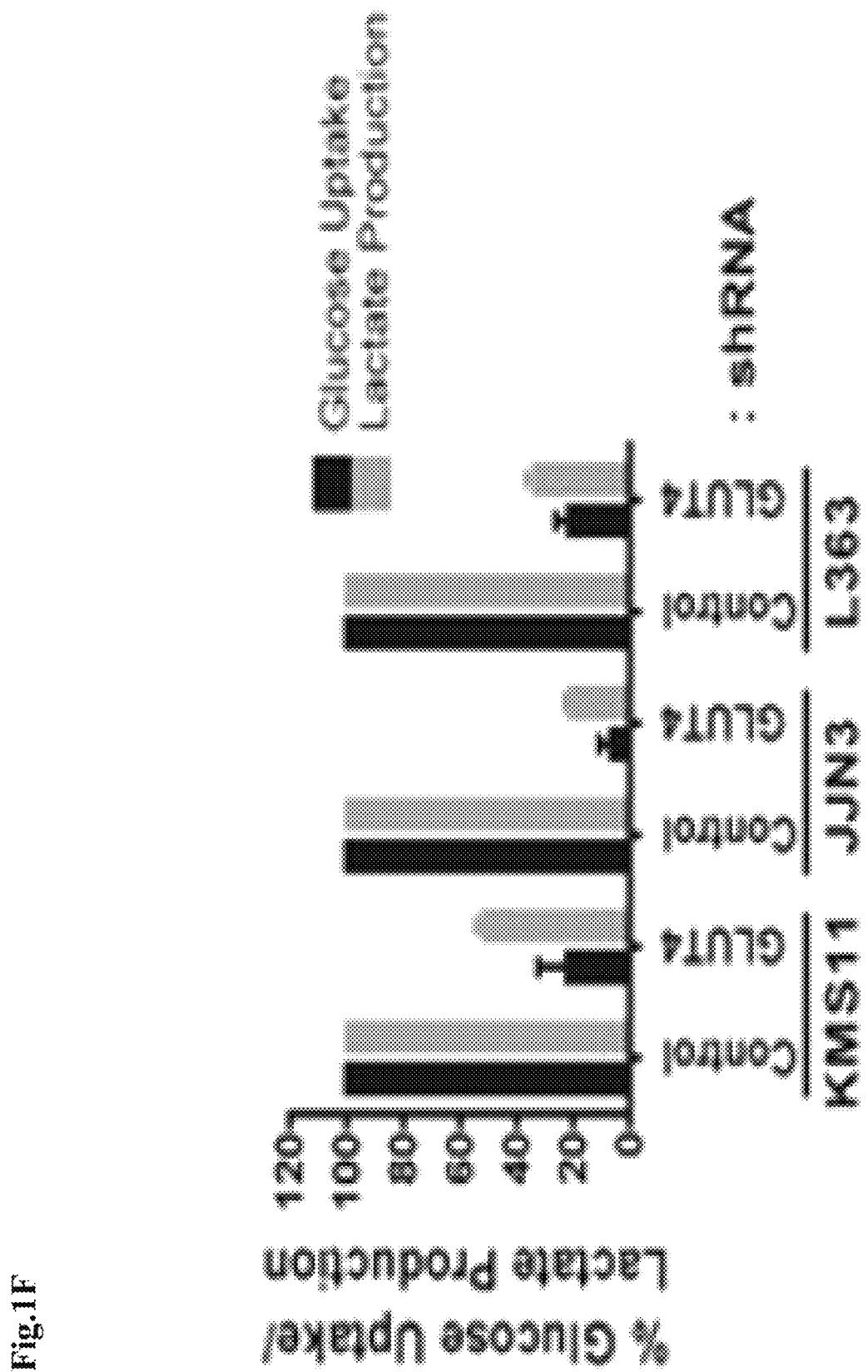
Figure 1G:
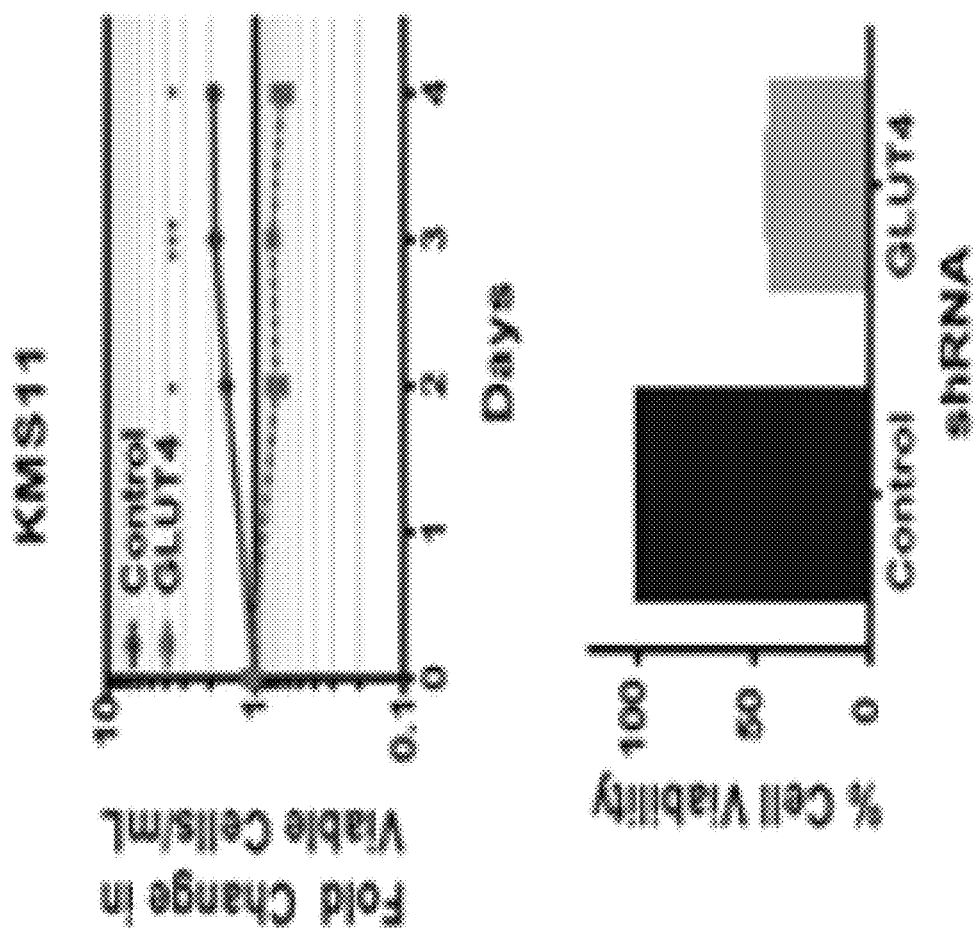
Figure 1H:
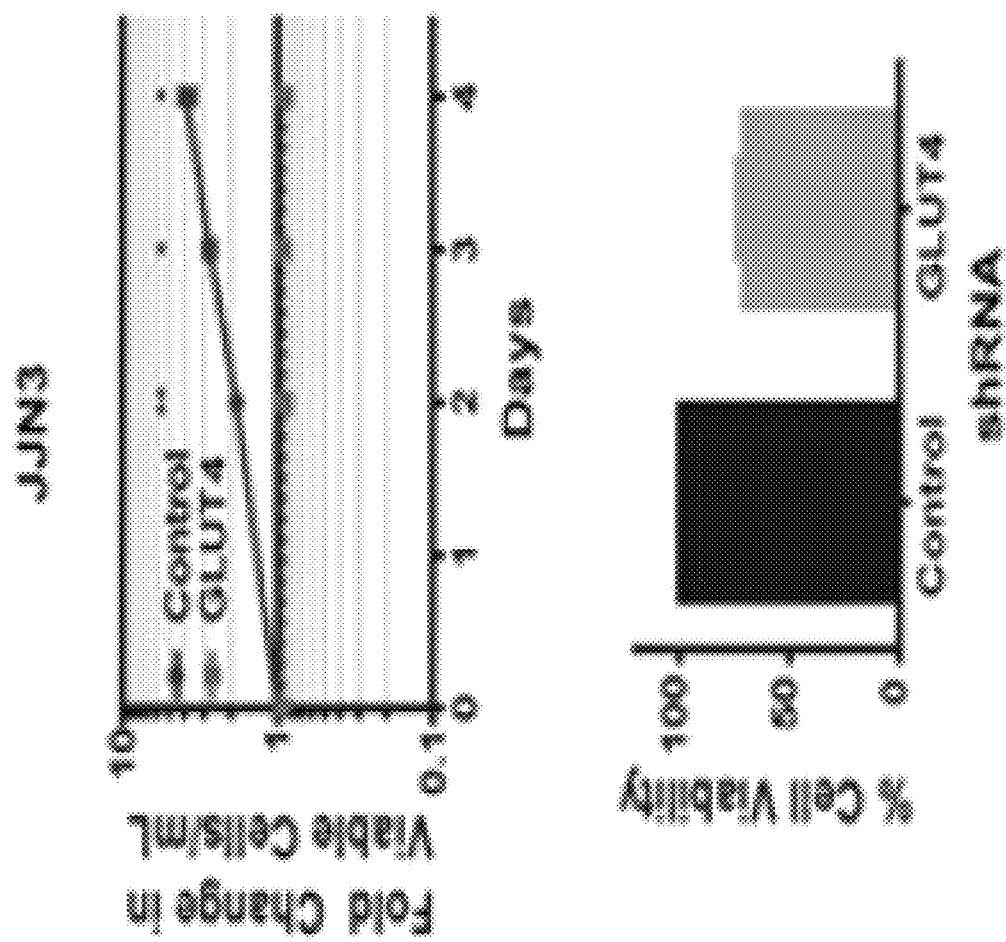
Figure 11:
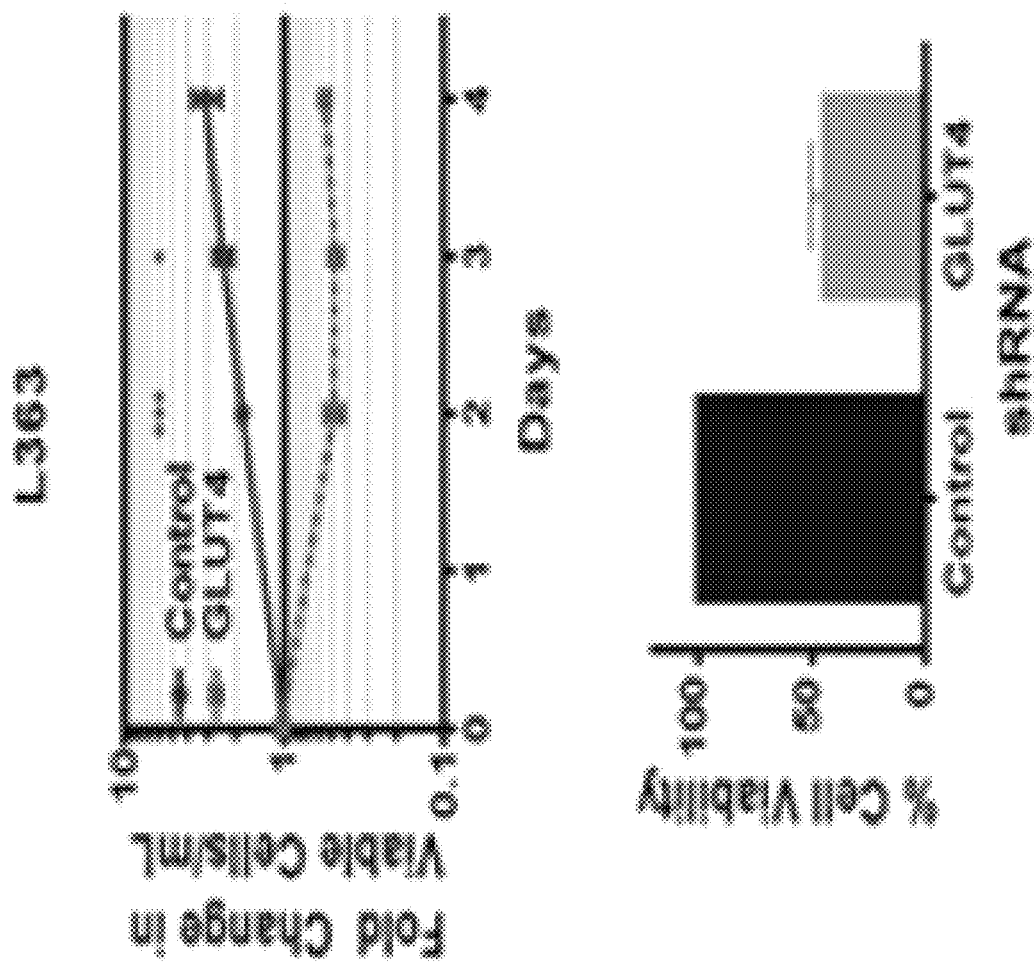
FIG. 11. Impact of ritonavir and/or metformin on viability of neuroblastoma cell lines. Cells were treated for 72 hrs with RIT (20 uM) and/or MET (5 mM) and cell viability was assessed by Annexin V/DAPI.
Figure 1J:
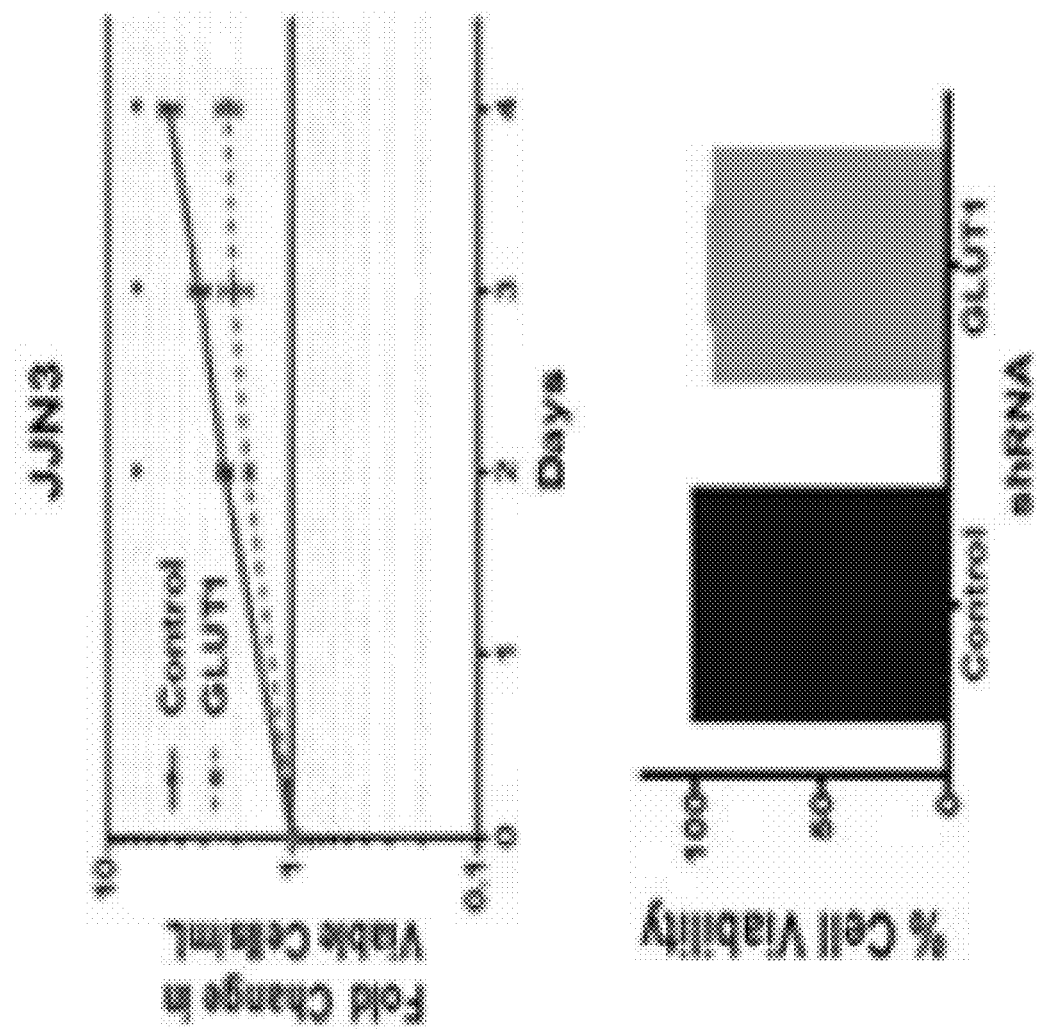

MM viability, proliferation and chemoresistance are maintained by continuous glucose catabolism. The majority of MM cells in contrast to normal B cells exhibit cell death when cultured in glucose-free media (FIG. 1A) and all MM cells exhibit growth inhibition (FIG. 1B). We detect overt cell death in cell lines like L363 and KMS11 (referred to as "sensitive") or minimal cell death such as detected in JJN3 and U266 cells (referred to as "resistant"). In addition, glucose-free culture sensitizes resistant U266 cells to a commonly used DNA damaging therapeutic doxorubicin, while normal PBMC are not impacted either by glucose-free culture or by treatment with doxorubicin (FIG. 1C-D), underscoring the utility of targeting glucose utilization for selective chemosensitization of MM. The elicitation of sensitivity to glucose-free culture are recapitulated upon knockdown (KD) of GLUT4 (FIG. 1G-I). GLUT4 KD demonstrated by immunoblotting (FIG. 1E) was associated with coordinate reduction in glucose uptake and lactate production (FIG. 1F). Importantly, GLUT1 KD did not impact proliferation of JJN3 cells to the same extent as GLUT4 KD (FIG. 1. Compare panels H and J). GLUT4 is therefore critical for maintaining glucose entry and viability in MM. We also tested an FDA approved compound, ritonavir, which is an HIV protease inhibitor that has an off-target inhibitory effect on GLUT4 [14]. Our recently published study demonstrates that ritonavir recapitulates the phenotypes elicited upon GLUT4 KD and glucose-free culture of MM cells[13].

Figure 2:
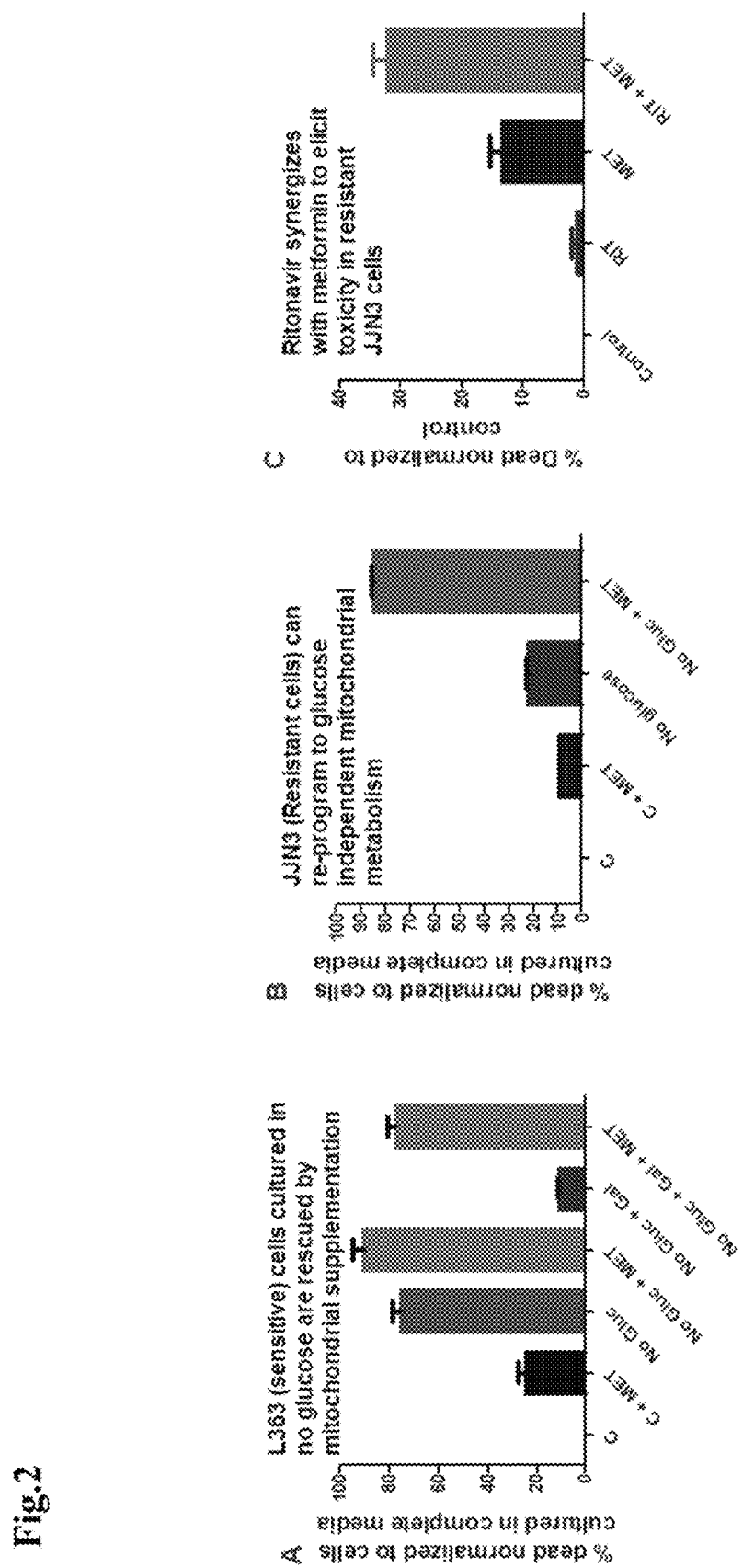
FIG. 2. Resistant MM re-program to mitochondrial metabolism resisting apoptosis upon glucose deprivation. MM cell lines were treated for 72 hrs in media containing glucose (control) or in the absence of glucoses with the following additions: ritonavir (20 μmolar) (RIT) metformin 5 mM (MET) or galactose 10 mM (Gal) and analyzed for viability by Annexin % DAPI staining. n=3±SEM.

Glucose-deprivation/ritonavir resistant mm can be targeted by co-treatment with mitochondrial complex 1 inhibitor metformin. To investigate whether mitochondrial oxidative phosphorylation can render MM cells resistant to glucose-deprivation we treated cells with metformin. which is a known mitochondrial complex 1 inhibitor [25-27]). Glucose deprived MM cells are sensitized to metformin, and galactose, which is a pentose phosphate pathway and mitochondrial substrate, significantly rescues viability of L363 cells cultured in the absence of glucose (FIG. 2A). To further confirm that galactose rescue of glucose-deprived cells was indeed due to rescue of mitochondrial metabolism, glucose-deprived L363 cells that were treated with galactose were also treated with metformin. Treatment with metformin reverses the metabolic rescue provided by galactose confirming the potential for mitochondrial substrates to rescue glucose-deprivation elicited toxicity in sensitive MM (FIG. 2A). To examine whether mitochondrial metabolism enabled resistant JJN3 cells to remain viable upon glucose deprivation, we treated JJN3 cells cultured in the absence of glucose with the complex 1 inhibitor, metformin (FIG. 2B), and glucose deprived JJN3 cells were observed to be sensitized to metformin. These observations strongly suggest a role for a mitochondrial metabolism in supplementing JJN3 cell viability upon glucose deprivation. Lastly, we tested whether the combination of ritonavir, which targeting GLUT4, in combination with metformin, which blocks mitochondrial complex 1 activity, can synergize to elicit cell death. As evident in FIG. 2C, co-treatment with ritonavir and metformin effectively induces apoptosis in the resistant, JJN3 cells.

Figure 3:
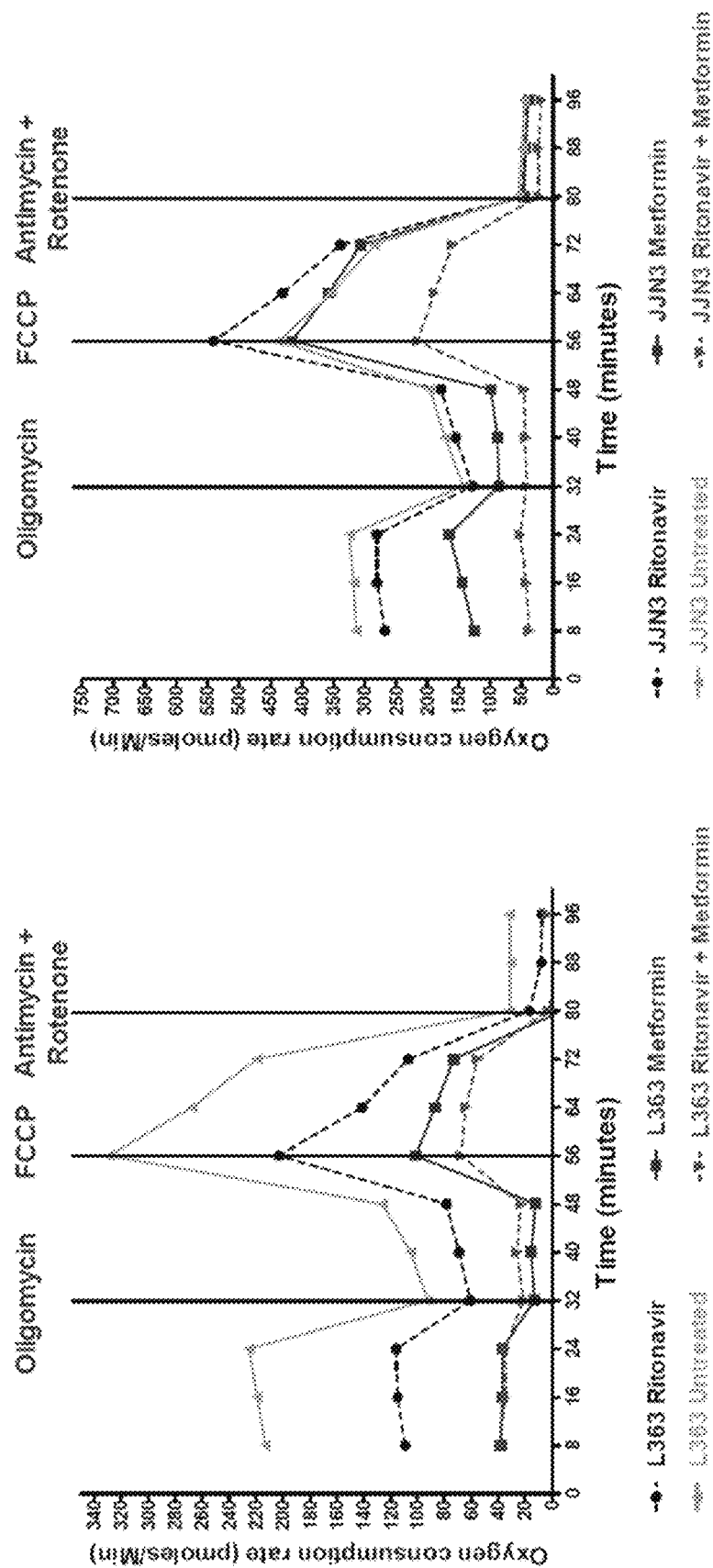
FIG. 3. Ritonavir and metformin effectively uncouple ATP synthesis and significantly reduce OCR in MM cells. L363 and JJN3 cells were treated with ritonavir (20 uM), metformin (5 mM) or the combination for 17 his and then oxygen consumption rate (OCR) was evaluated using a SeaHorse XF24 bioanalyzer. Cellular viability was assessed before OCR measurements and 400,000 viable cells were plated in 5 replicates. Result is representative of an n=3.

Ritonavir treated JJN3 cells switch to mitochondrial metabolism as evident by an increase in oxygen consumption rate. To further confirm that the resistance of JJN3 cells to ritonavir/glucose-deprivation elicited toxicity was due to maintenance of mitochondrial metabolism in the JJN3 cells, we measured oxygen consumption rate (OCR) over time using the SeaHorse bioenergetics analyzer (FIG. 3). The treatment of L363 and JJN3 cells with ritonavir leads to a significant reduction in OCR in the sensitive cells. However the resistant JJN3 cells exhibit significant reduction in OCR only when co-treated with metformin (FIG. 3). The combinatorial treatment effectively uncouples ATP synthesis from OXPHOS correlating with cell death.

Figure 4:
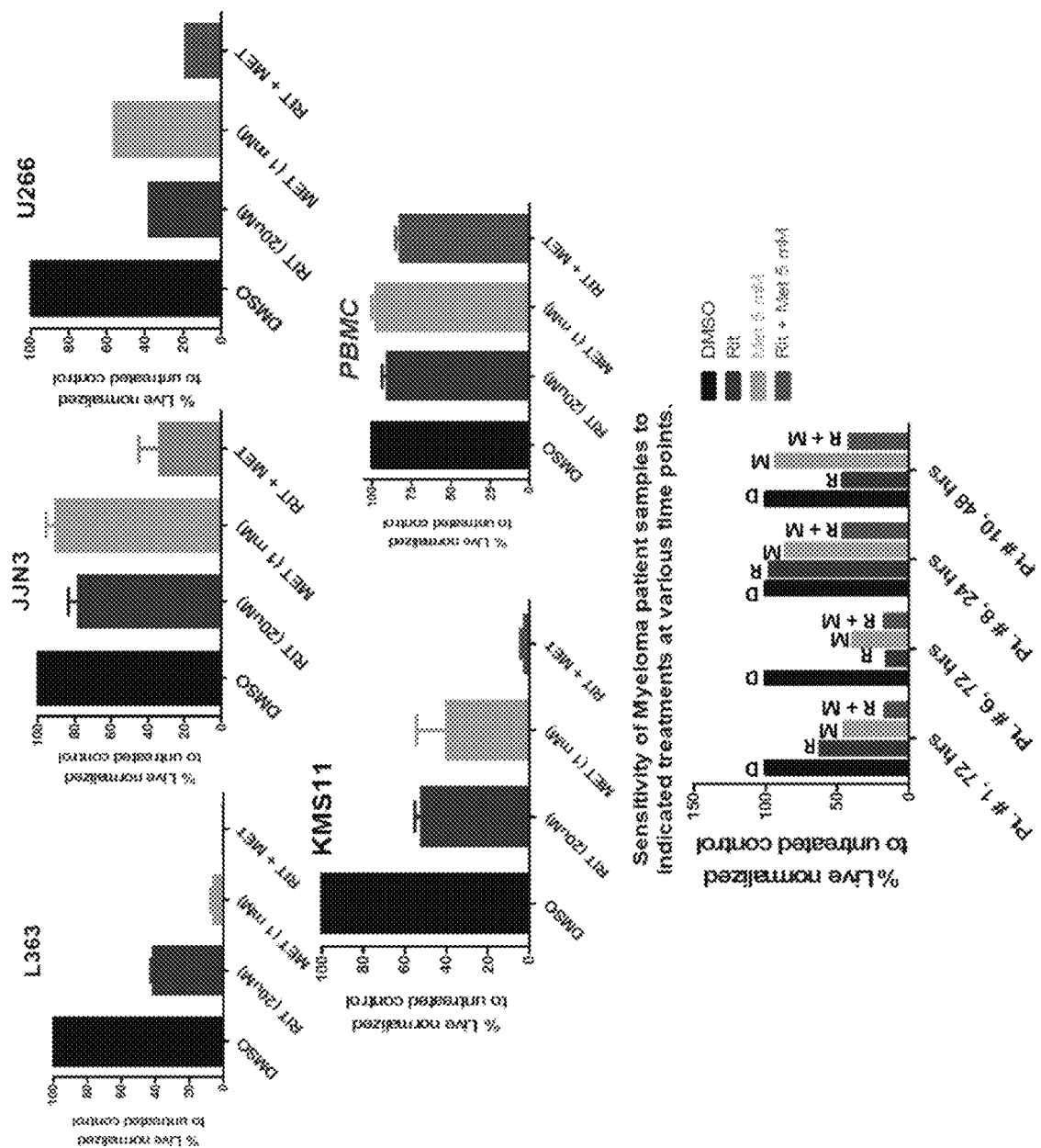
FIG. 4. L363, JJN3, U266, and KMS11 MM lines treated with ritonavir are sensitized to lower dose of metformin (MET) while normal PBMC do not exhibit cytotoxicity. Cells were treated for 72 hrs with 20 μM RIT or 1 mM MET as indicated below bars. Impact on proliferation was assessed by an MTS assay in cell lines while PMBC cytotoxicity and patient sample cytotoxicity was evaluated by AnnexinV/DAPI staining.

Ritonavir synergizes with metformin to impact viability across all mm cell lines with no impact on normal pbmc. The concentration of ritonavir used in our in vitro studies (i.e., 20 uM) is close to the 16 uM $C_{max}$ plasma concentration achieved in humans [28]. Current metformin dosing regimens in humans have been shown to have anti-cancer properties [21,22]. We sought to determine if lower concentrations of metformin could also synergize with ritonavir to elicit toxicity. Additional MM lines, both sensitive and resistant, were evaluated for sensitivity to ritonavir in combination with a dose range of metformin (FIG. 4). Viability of cells was determined 72 hrs post treatment by an MTS proliferation assay. Our data suggests that even lower doses of metformin are effective in synergizing with ritonavir to elicit toxicity. Additionally, MM primary patient samples and normal PBMC were evaluated for sensitivity to these compounds and tumor-selective cytotoxicity of ritonavir and metoformin was observed (FIG. 4).

Figure 5:
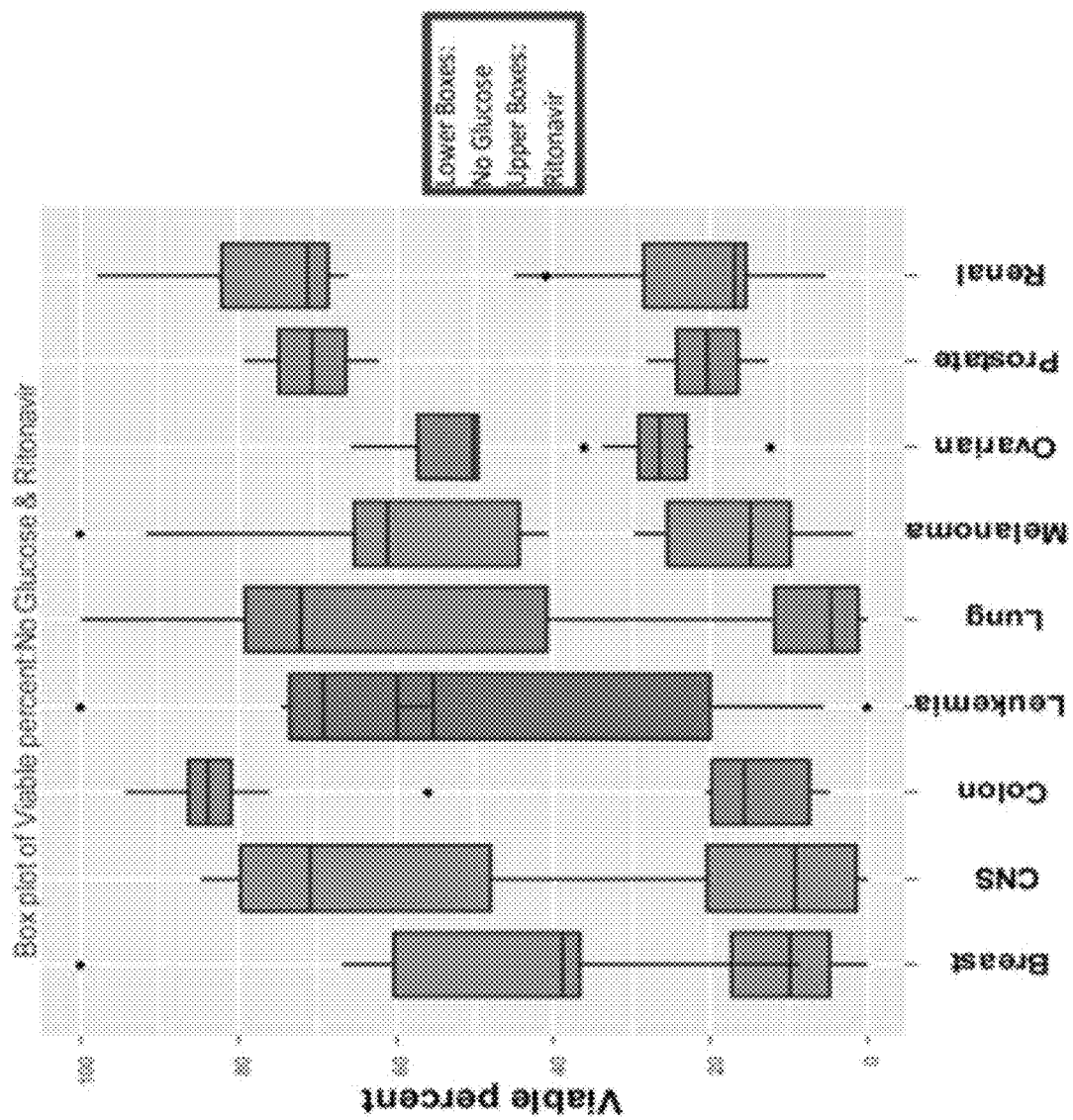
FIG. 5. NCI-60 cell lines are variably responsive to glucose deprivation (lower boxes) or ritonavir, 20 μM, (upper boxes). 48 hr MTS assay, n=3+/−SEM, p<0.05

GLUT4 activity may be prevalent across multiple cancers. To examine the dependency of other cancers on GLUT4 activity, we utilized the NCI-60 cancer cell line panel. NCI-60) cells were cultured either in the absence of glucose or treated with 20 uM ritonavir for 48 hours followed by analysis of viability by MTS assay. Our hypothesis is that cancers dependent on GLUT4 activity should show similar responses to ritonavir treatment as with that detected upon culture in glucose-free media. The box plots in FIG. 5 for each cancer group of the NCI-60 panel suggest that viability of all NCI-60 cell lines are impacted significantly by glucose-free culture. A coordinate sensitivity to ritonavir, which is defined as a median reduction of viability by 50% or greater, is clearly detected in breast, melanoma and ovarian cancers. The NCI-60 lines are representative of genetic heterogeneity within each cancer group. Therefore, it is possible that we may detect a role for GLUT4 in a subset of cancers within each group connected to a specific genotype. These results warrant further investigation into the reliance of breast, melanoma and ovarian cancers on GLUT4 activity/localization and sensitivity to co-treatment with ritonavir and metformin.

Figure 6:
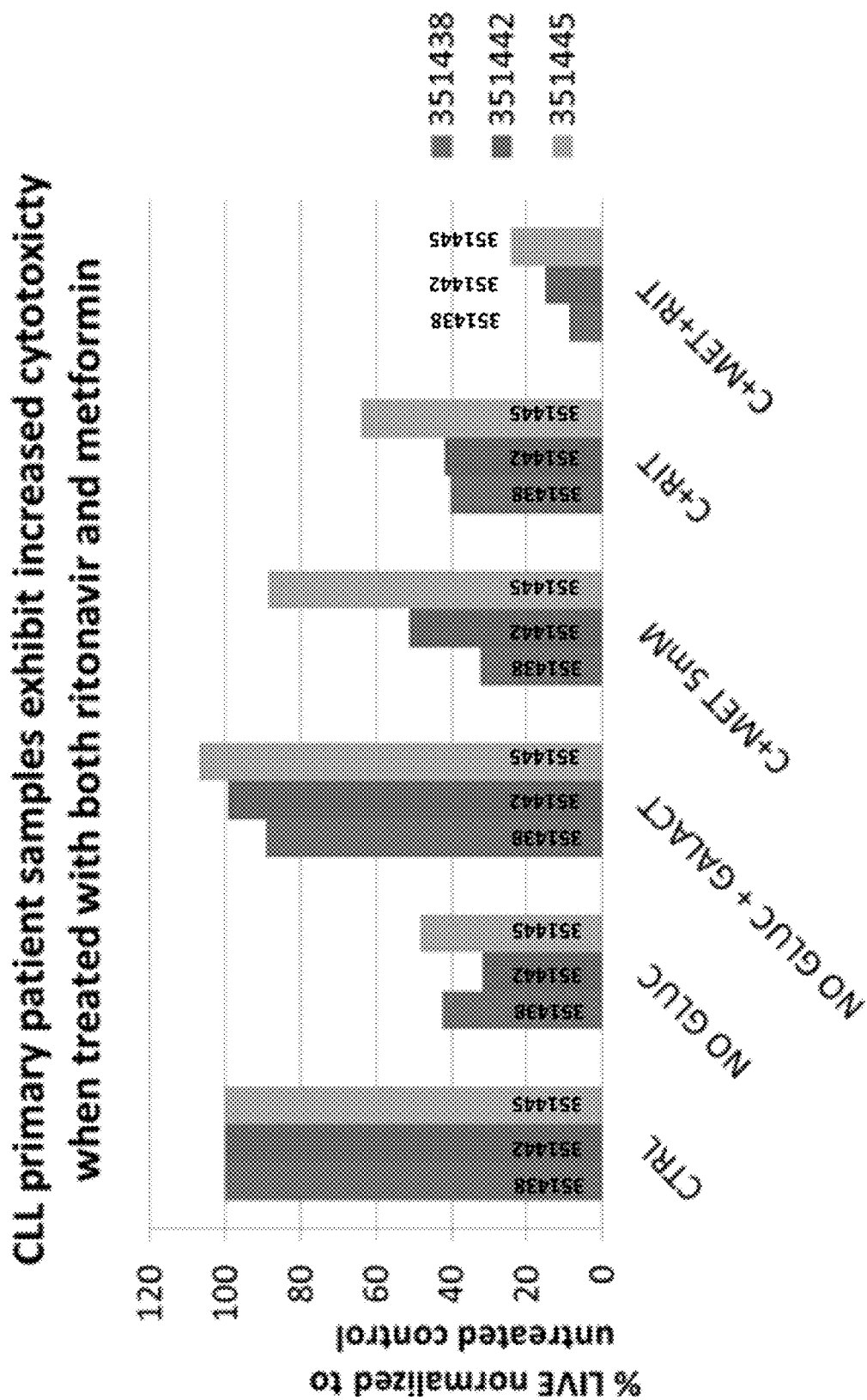
FIG. 6. CLL primary patient samples exhibit mitochondrial metabolism that is rescued by treatment of glucose-deprived cells (No gluc) with galactose. Combination of RIT (20 uM) and MET (5 mM) elicits potent toxicity in cells cultured in complete media "C". Cells were treated for 72 hrs with indicated combinations and cell viability assessed by Annexin/DAPI staining and flow cytometry.
Figure 7:
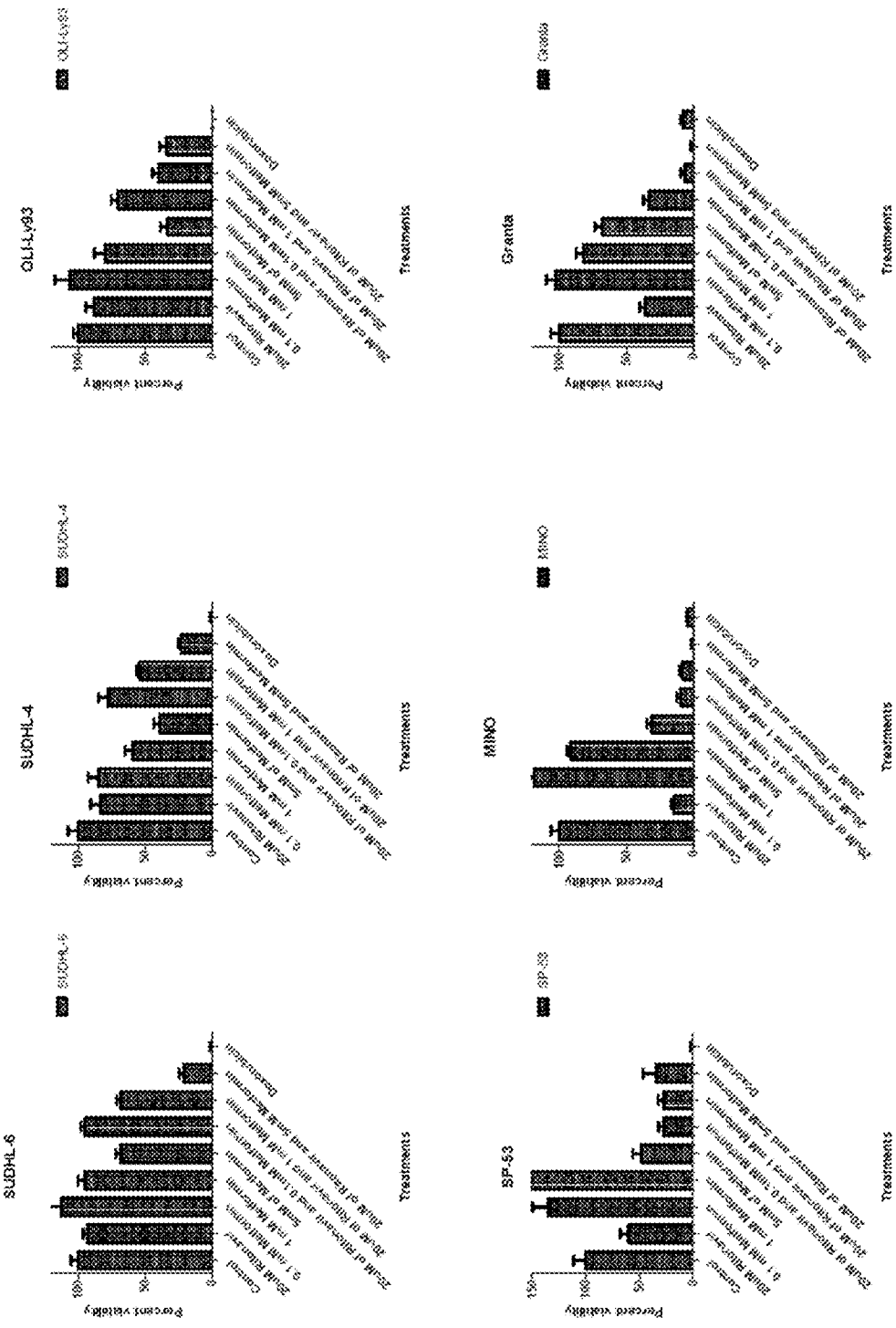
FIG. 7. Impact of ritonavir and/or metformin on viability/proliferation of DLBC and Mantle cancer cell lines. Combination of RIT (20 uM) and MET (5 mM) elicits potent toxicity in cells cultured in complete media "C". Cells were treated for 72 hrs with indicated combinations and cell viability/proliferation was assessed by MTS assay at 72 hrs.
Figure 8:
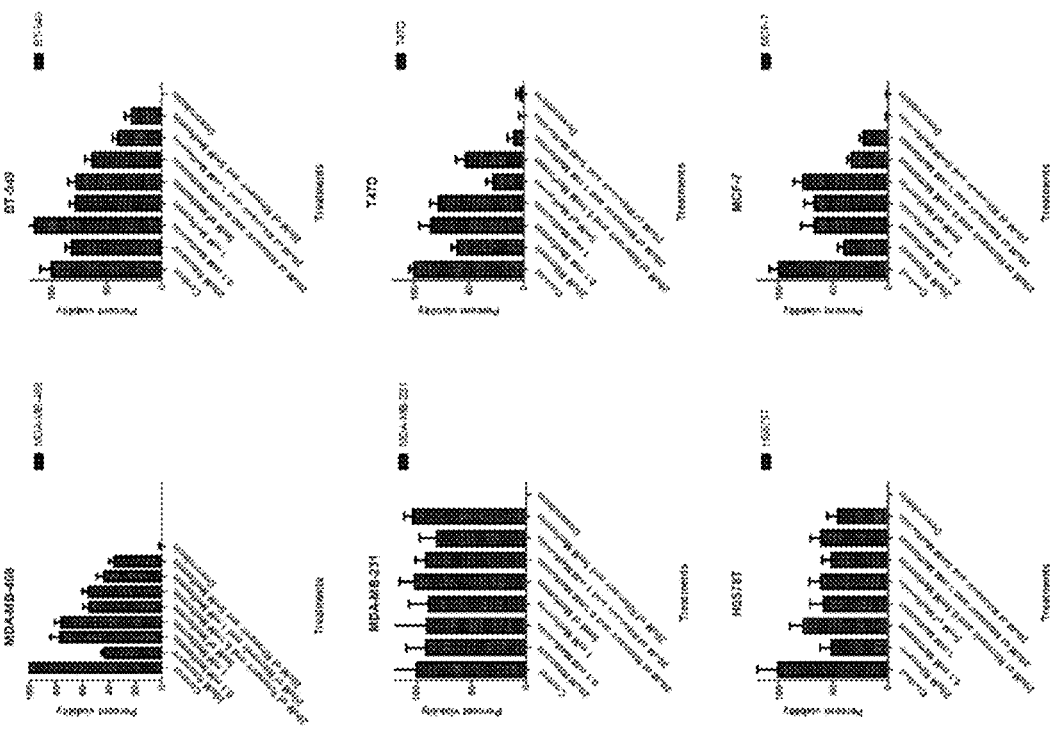
FIG. 8. Impact of ritonavir and/or metformin on viability/proliferation of breast cancer cell lines. Combination of RIT (20 uM) and MET (5 mM) elicits potent toxicity in cells cultured in complete media "C". Cells were treated for 72 hrs with indicated combinations and cell viability/proliferation was assessed by MTS assay at 72 hrs.
Figure 9:
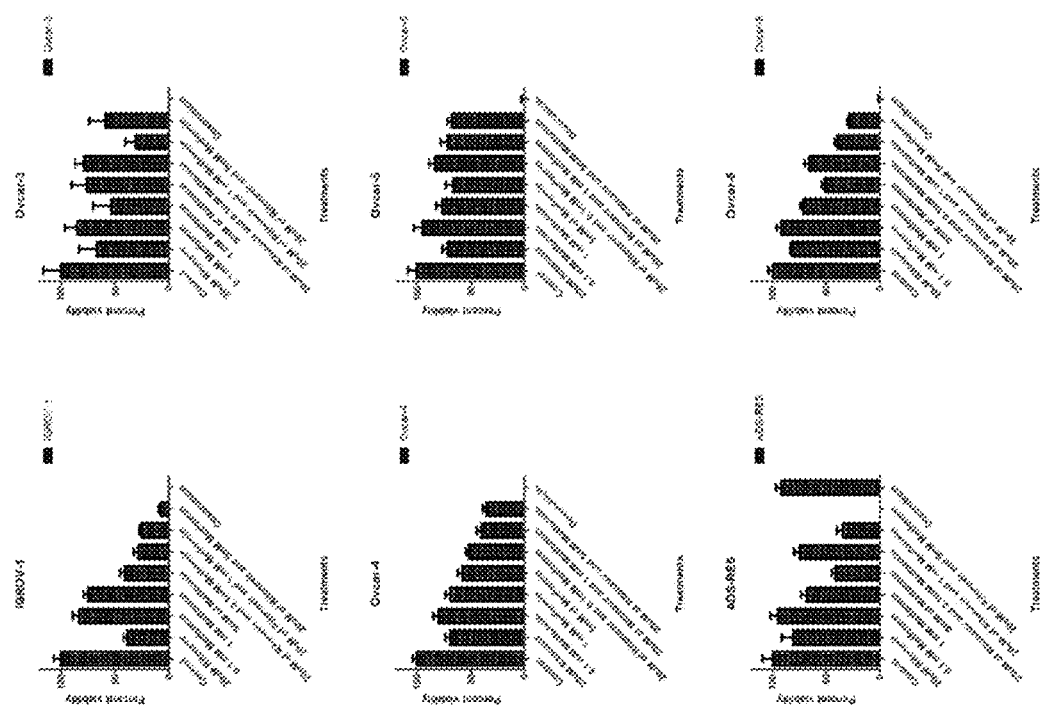
FIG. 9. Impact of ritonavir and/or metformin on viability/proliferation of ovarian cancer cell lines. Combination of RIT (20 uM) and MET (5 mM) elicits potent toxicity in cells cultured in complete media "C". Cells were treated for 72 hrs with indicated combinations and cell viability/proliferation was assessed by MTS assay at 72 hrs.
Figure 10:
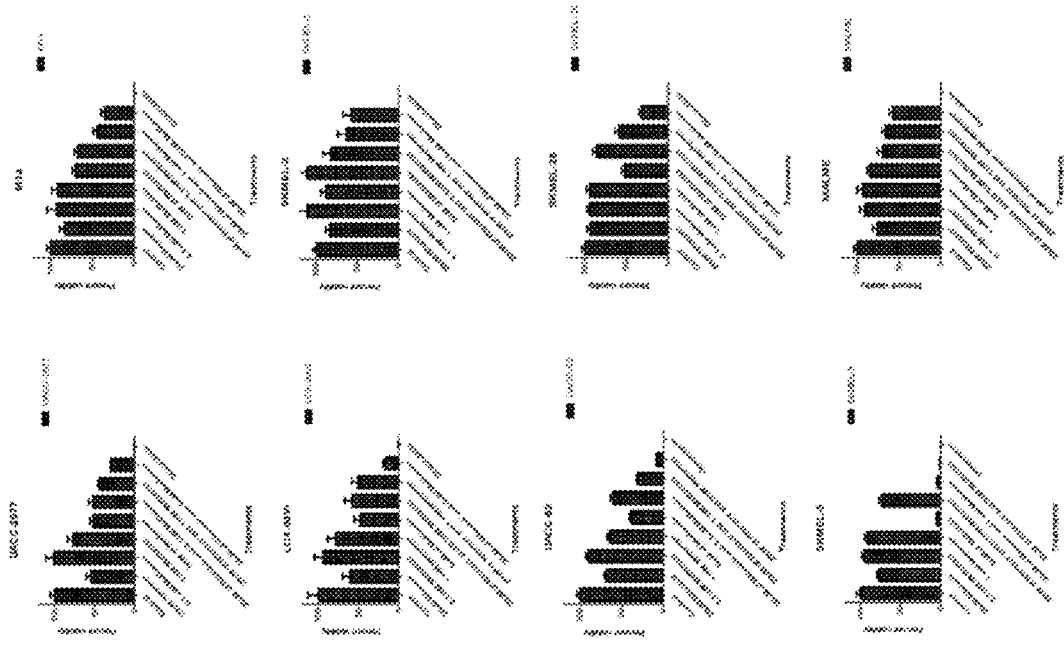
FIG. 10. Impact of ritonavir and/or metformin on viability/proliferation of melanoma human cancer cell lines. Combination of RIT (20 uM) and MET (5 mM) elicits potent toxicity in cells cultured in complete media "C". Cells were treated for 72 hrs with indicated combinations and cell viability/proliferation was assessed by MTS assay at 72 hrs.

Primary chronic lymphocytic leukemia (CLL) patient samples exhibit dependence on glucose utilization and mitochondrial metabolism that can be targeted by co-treatment with ritonavir and metformin. We are extending our examination of the utility of ritonavir and metformin in primary patient CLL and MM patient samples. We have previously published on the efficacy of glucose-deprivation and ritonavir treatment in MM patient samples and now demonstrate the efficacy of the ritonavir-metformin co-treatment regimen in CLL patient samples (FIG. 6). We further tested the impact of ritonavir and metformin co-treatment in breast, melanoma, ovarian, DLBCL, mantle cell and neuroblastoma cell lines. As demonstrated in FIGS. 7-11, the treatment of a number of these cell lines with a combination of ritonavir and metformin resulted in a significant loss in cell viability.

Figure 12:
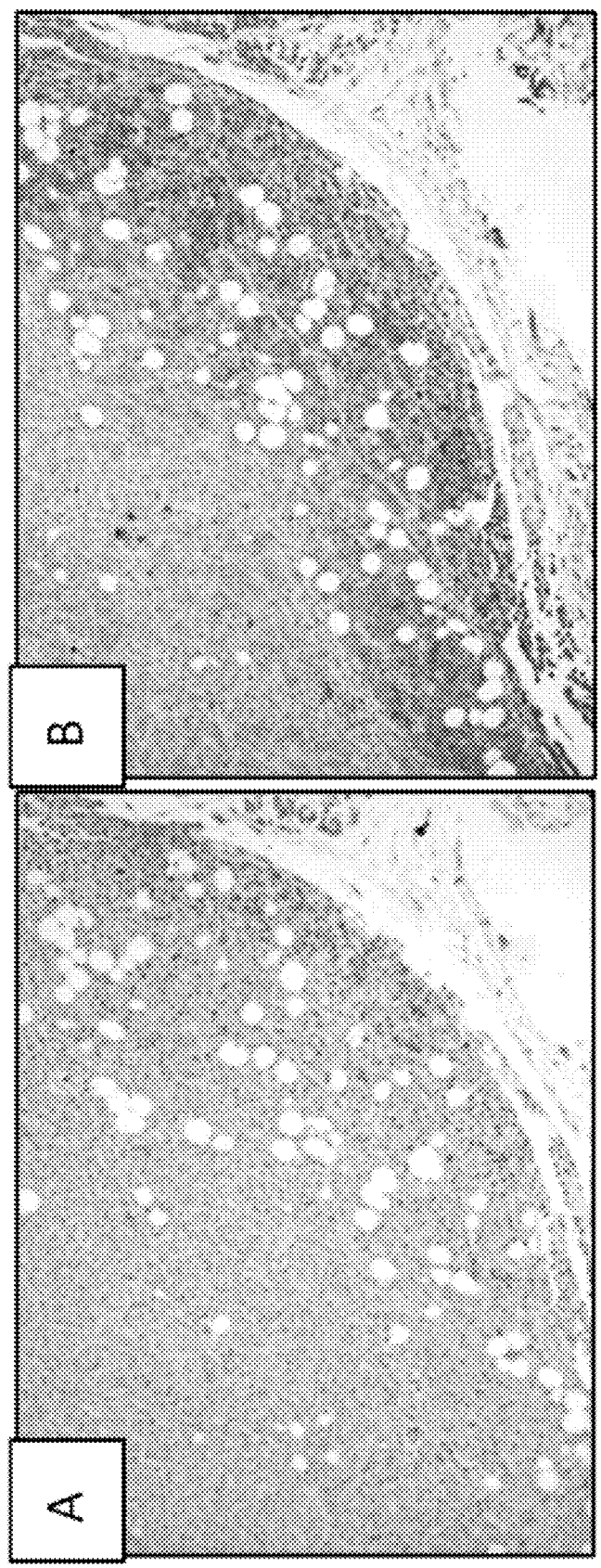
FIG. 12. KMS11 myeloma xenograft tumors were stained for GLUT1 (panel A) or GLUT4 (panel B). GLUT4 is staining is particularly elevated at the leading edge of the tumor while GLUT1 is undetected.
Figure 13A:
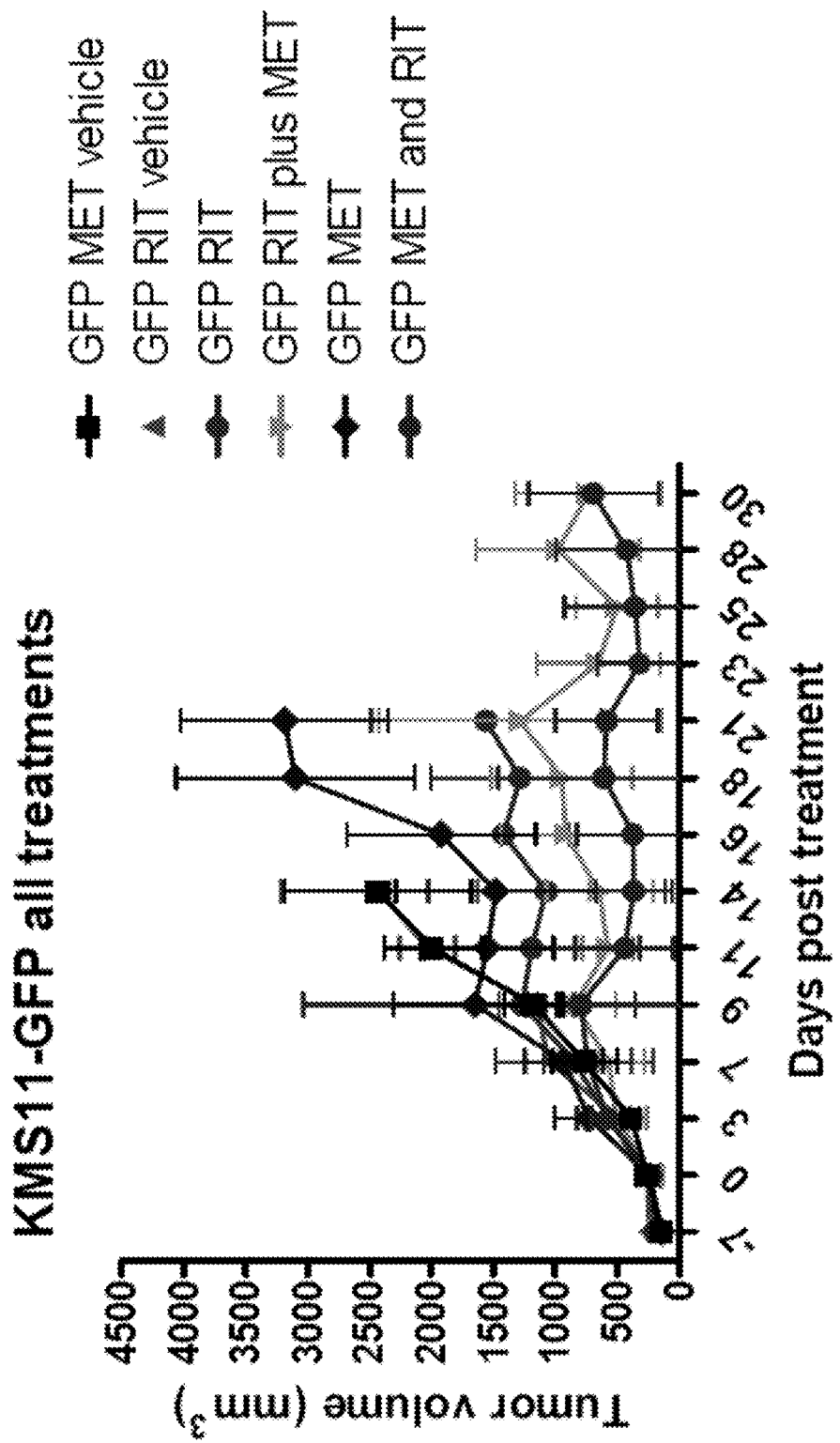
FIG. 13. Impact of ritonavir and/or metformin on in vivo growth of KMS11 myeloma xenograft tumors. Ritonavir was administered at 50 mgs/kg by oral gavage and metformin was administered at 125 mgs/kg by ip injection. Both compounds were administered under a daily regimen, one week after palpable tumors were detected. (A) tumor volume; (B) tumor weight (C) percent reduction in tumor weight; and (D) Kaplan-Meier plot of survival of mice bearing KMS11-GFP tumors.
Figure 13B:
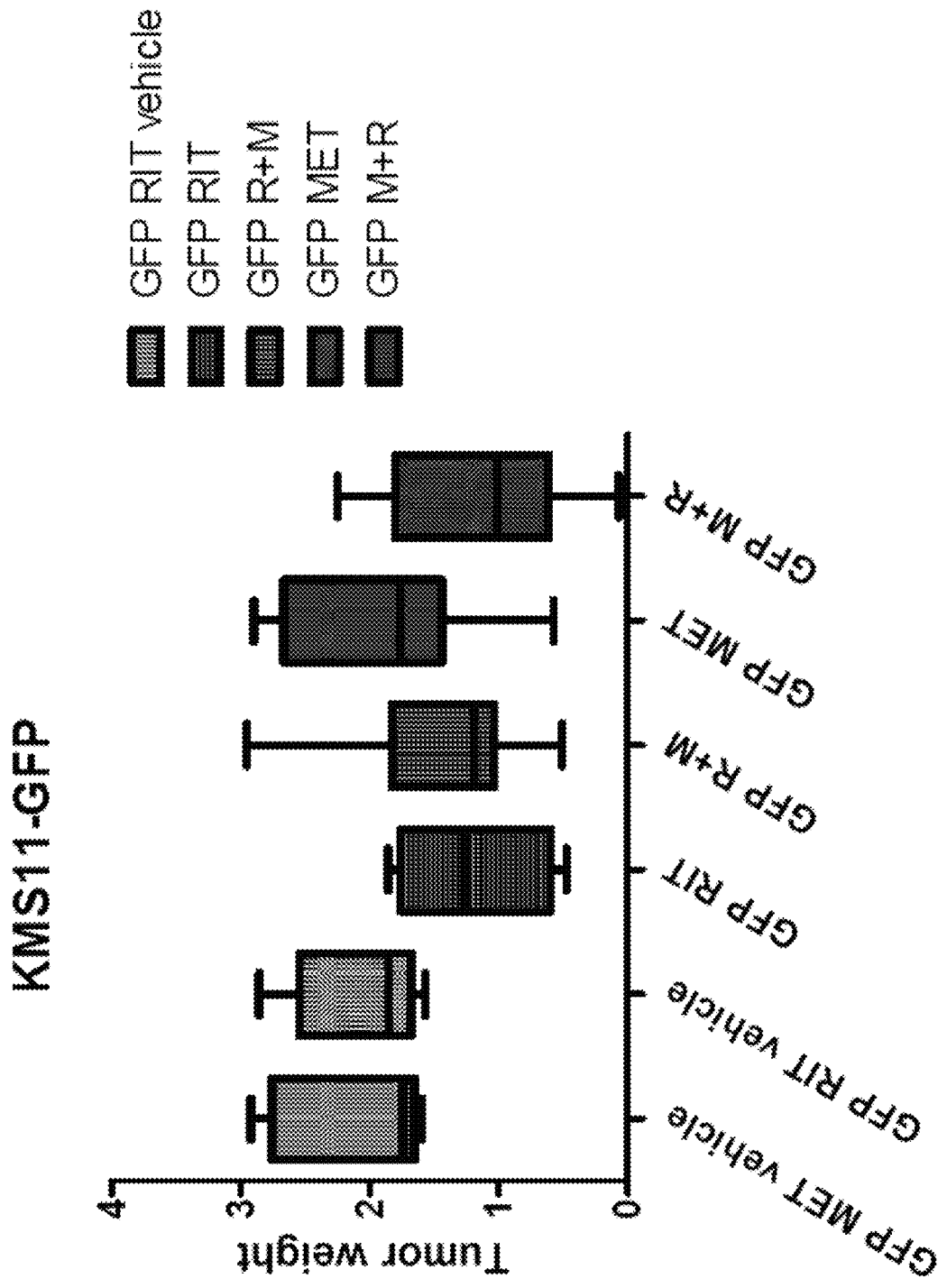
Figure 13C:
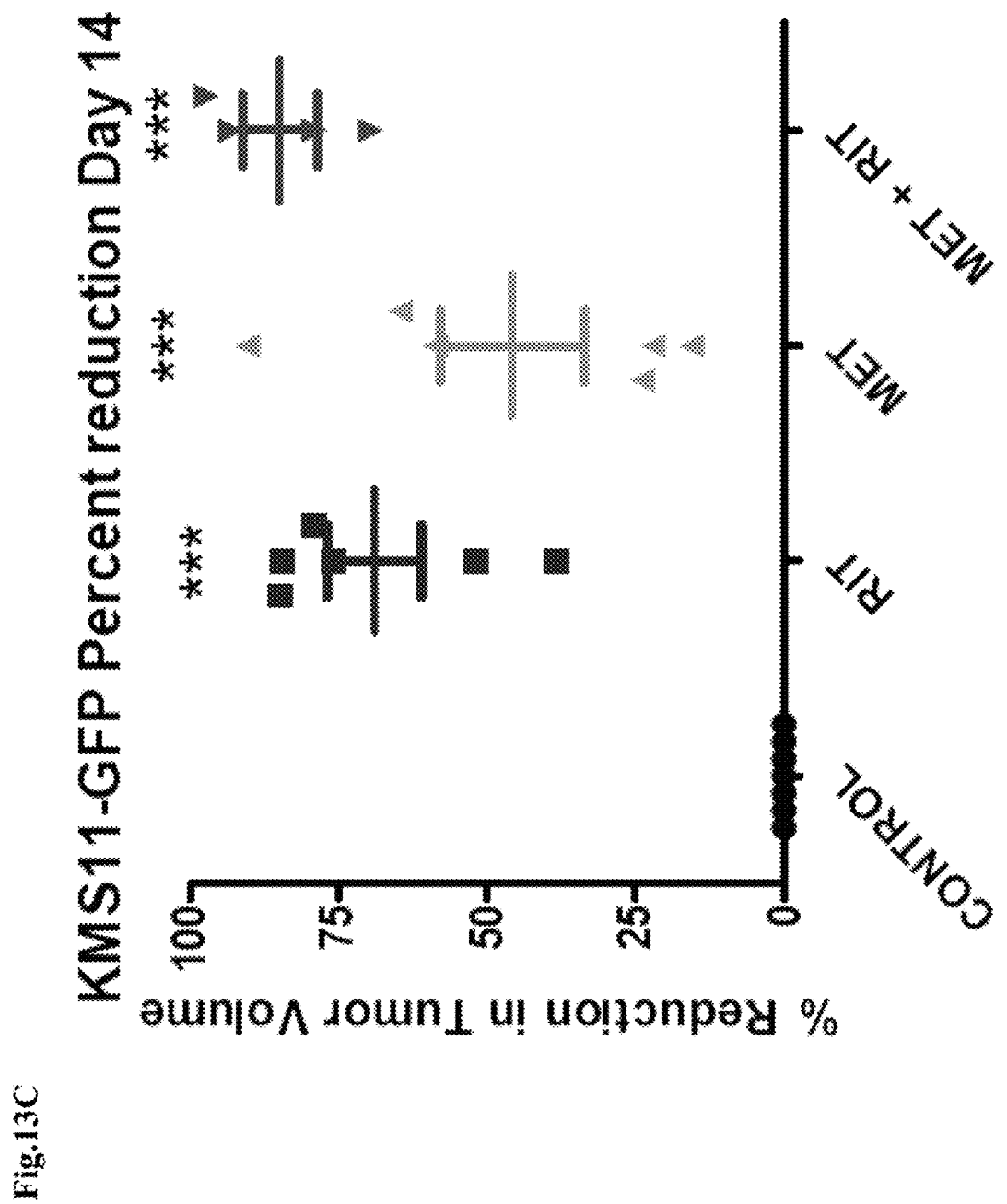
Figure 13D:
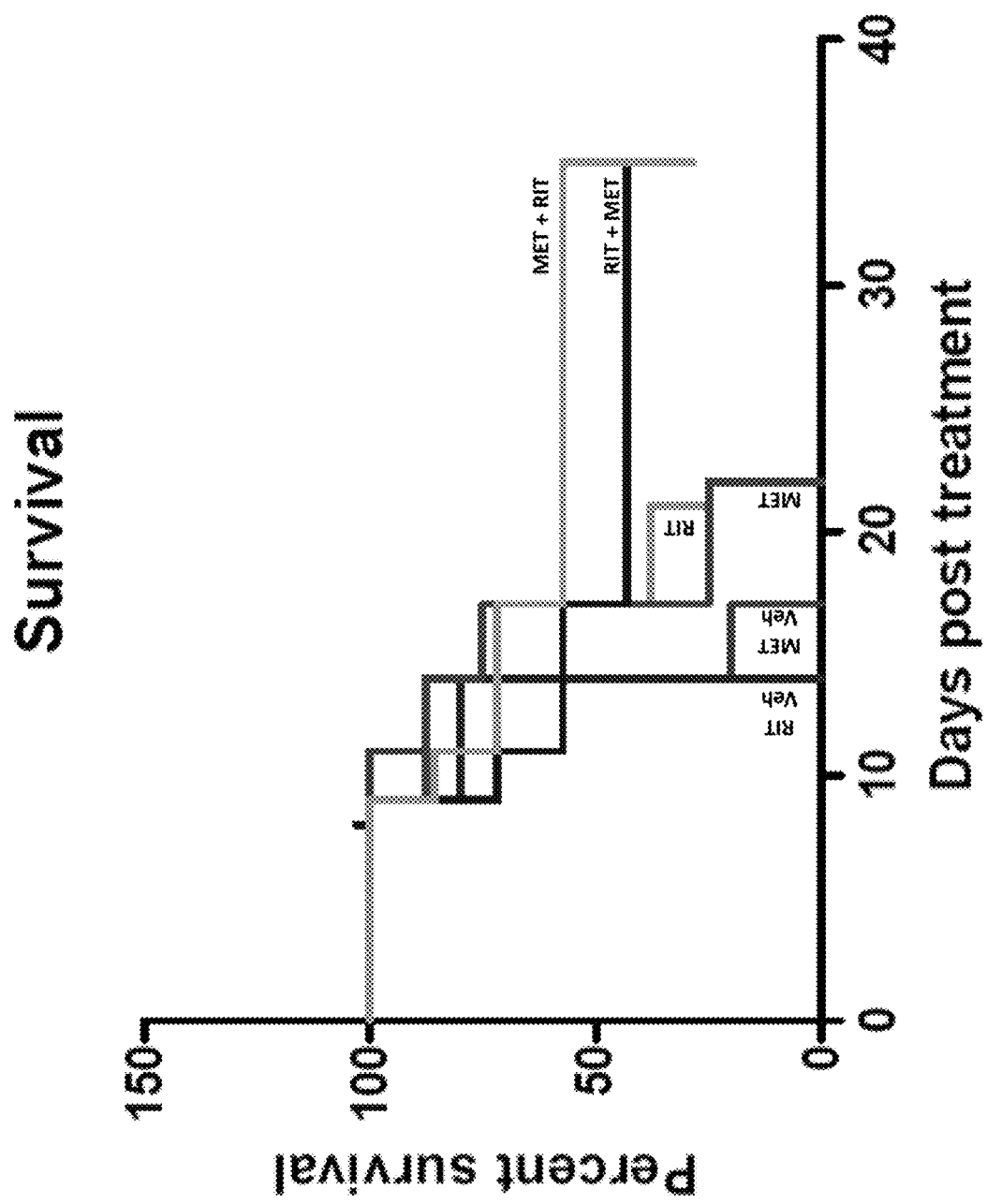

Human myeloma xenograft tumors exhibit more GLUT4 at the leading proliferative edge of the tumor. The ritonavir metformin combination is also effective in myeloma xenograft tumors. Representative image of a KMS11 MM human cell line xenograft tumor stained for GLUT and GLUT4 is shown in FIG. 12 demonstrating increased GLUT4 expression at the leading edge of the tumor. Positive staining controls for GLUT1 and GLUT4 were established with these antibodies (data not shown).

The combinatorial treatment regimen of metformin with ritonavir was effective in improving progression free survival and reducing myeloma xenograft tumor burden FIG. 13. Xenograft tumors were generated by introduction of KMS11 cells into mice, once tumors were palpable mice were administered ritonavir by oral gavage at 50 mgs/kg/day and/or metformin by ip injection at 125 mgs/kg/day. As indicted in FIG. 10, the volume and weight of xenographic tumors was significantly reduced in mice treated with both ritonavir and metformin. Further, mice that were treated with both ritonavir and metformin exhibited longer survival times.

Summary

Our studies reveal the promise of a potent combinatorial regimen involving FDA approved ritonavir or other GLUT4 targeting agents and metformin for the treatment of MM and potentially other malignancies such as CLL, breast, melanoma, ovarian and neuroblastoma cancers. With ritonavir, which targets glucose transport and metformin which targets resistance-promoting compensatory mitochondrial metabolism that are up-regulated upon inhibition of glucose transport, the two FDA approved drugs can be re-purposed for combinatorial therapy to inhibit tumor cell metabolism and elicit potent lethality.

REFERENCES

1. Richardson, P. G., et al., New treatments for multiple myeloma. Oncology (Williston Park), 2005. 19(14): p. 1781-92; discussion 1792, 1795-7.

2. Munshi, N., Plasma cell disorders: an historical perspective. Hematology, 2008. 2008: p. 297.

3. Warburg, O., On the origin of cancer cells. Science, 1956. 123(3191): p. 309-14.

4. Gatenby, R. A. and R. J. Gillies, Why do cancers have high aerobic glycolysis? Nat Rev Cancer, 2004. 4(11): p. 891-9.

5. Castellani, M., et al., The prognostic value of F-18 fluorodeoxyglucose bone marrow uptake in patients with recent diagnosis of multiple myeloma: a comparative study with Tc-99m sestamibi. Clin Nucl Med, 2010. 35(1): p. 1-5.

6. Durie, B. G., et al., Whole-body (18)F-FDG PET identifies high-risk myeloma. J Nucl Med, 2002. 43(11): p. 1457-63.

7. Bredella, M. A., et al., Value of FDG PET in the assessment of patients with multiple myeloma. AJR Am J Roentgenol. 2005. 184(4): p. 1199-204.

8. Bartel, T. B., et al., F18-fluorodeoxyglucose positron emission tomography in the context of other imaging techniques and prognostic factors in multiple myeloma. Blood, 2009. 114(10): p. 2068-76.

9. Zamagni, E., et al., Prognostic relevance of 18-FFDG PET/CT in newly diagnosed multiple myeloma patients treated with up-front autologous transplantation. Blood, 2011. 118(23): p. 5989-95.

10. Vander Heiden, M. G., et al., Growth factors can influence cell growth and survival through effects on glucose metabolism. Mol Cell Biol, 2001. 21(17): p. 5899-912.

11. Xu, R. H., et al., Inhibition of glycolysis in cancer cells: a novel strategy to overcome drug resistance associated with mitochondrial respiratory defect and hypoxia. Cancer Res, 2005. 65(2): p. 613-21.

12. Rodriguez-Enriquez, S., et al., Kinetics of transport and phosphorylation of glucose in cancer cells. J Cell Physiol, 2009. 221(3): p. 552-9.

13. McBrayer, S. K., et al., Multiple myeloma exhibits novel dependence on GLUT4, GLUT8, and GLUT11: implications for glucose transporter-directed therapy. Blood, 2012.

14. Murata, H., P. W. Hruz, and M. Mueckler, The mechanism of insulin resistance caused by HIV protease inhibitor therapy. J Biol Chem, 2000. 275(27): p. 20251-4.

15. Wuilleme-Toumi, S., et al. Mcl-1 is overexpressed in multiple myeloma and associated with relapse and shorter survival. Leukemia, 2005. 19(7): p. 1248-52.

16. Vyas, A. K., et al., Effects of the HIV protease inhibitor ritonavir on GLUT4 knock-out mice. J Biol Chem, 2010. 285(47): p. 36395-400.

17. Hertel, J., et al., A structural basis for the acute effects of HIV protease inhibitors on GLUT4 intrinsic activity. I Biol Chem, 2004. 279(53): p. 55147-52.

18. Carr, A., et al., A syndrome of peripheral lipodystrophy, hyperlipidaemia and insulin resistance in patients receiving HIV protease inhibitors. AIDS, 1998. 12(7): p. F51-8.

19. Hresko, R. C. and P. W. Hruz, HIV protease inhibitors act as competitive inhibitors of the cytoplasmic glucose binding site of GLUTs with differing affinities for GLUT1 and GLUT4. PLoS One, 2011. 6(9): p. e25237.

20. Evans, J. M., et al., Metformin and reduced risk of cancer in diabetic patients. BMJ, 2005. 330(7503): p. 1304-5.

21. Lai, S. W., et al., Antidiabetes drugs correlate with decreased risk of lung cancer: a population-based observation in Taiwan. Clin Lung Cancer, 2012. 13(2): p. 143-8.

22. MacKenzie, M. J., et al., A phase I study of temsirolimus and metformin in advanced solid tumours. Invest New Drugs, 2012. 30(2): p. 647-52.

23. Ben Sahra, I., et al., Metformin in cancer therapy: a new perspective for an old antidiabetic drug? Mol Cancer Ther, 2010. 9(5): p. 1092-9.

24. Kohli, R., et al., A randomized placebo-controlled trial of metformin for the treatment of HIV lipodystrophy. HIV Med, 2007. 8(7): p. 420-6.

25. Cheong. J. H., et al., Dual inhibition of tumor energy pathway by 2-deoxyglucose and metformin is effective against a broad spectrum of preclinical cancer models. Mol Cancer Ther, 2011. 10(12): p. 2350-62.

26. Owen, M. R., E. Doran, and A. P. Halestrap, Evidence that metformin exerts its anti-diabetic effects through inhibition of complex 1 of the mitochondrial respiratory chain. Biochem J. 2000. 348 Pt 3: p. 607-14.

27. El-Mir, M. Y., et al., Dimethylbiguanide inhibits cell respiration via an indirect effect targeted on the respiratory chain complex 1. J Biol Chem, 2000. 275(1): p. 223-8.

28. Hsu, A., et al., Multiple-dose pharmacokinetics of ritonavir in human immunodeficiency virus-infected subjects. Antimicrob Agents Chemother, 1997. 41(5): p. 898-905.

In the foregoing description, certain terms have been used for brevity, clearness, and understanding. No unnecessary limitations are to be implied therefrom beyond the requirement of the prior art because such terms are used for descriptive purposes and are intended to be broadly construed. The different compositions and method steps described herein may be used alone or in combination with other compositions and method steps. It is to be expected that various equivalents, alternatives and modifications are possible. The cited patent and non-patent references are incorporated by reference in their entireties. The definitions provided in the present specification supersede any definition for a term provided in a cited reference.

The invention claimed is:

1. A method comprising: (a) requesting a test providing results of an analysis to detect GLUT4 in cancer cells from a biological sample obtained from a patient diagnosed with multiple myeloma, chronic lymphocyte leukemia (CLL), diffuse large B-cell lymphoma (DLBCL), mantle cell lymphoma, neuroblastoma, breast cancer, or ovarian cancer, and (b) administering a GLUT4 inhibitor and an OXPHOS inhibitor to the patient if an elevated level of the GLUT4 in the cancer cells is detected or if the GLUT4 is mislocalized in the cancer cells, wherein the GLUT4 inhibitor is selected from ritonavir and indinavir and the OXPHOS inhibitor is selected from metformin, phenformin, buformin, and pharmaceutically acceptable salts thereof.

2. The method of claim 1, wherein the mislocalization comprises increased localization of GLUT4 to the plasma membrane of the cancer cells.

3. The method of claim 1, wherein the GLUT4 inhibitor is selected from ritonavir and the OXPHOS inhibitor is metformin.

4. A method of treating multiple myeloma, chronic lymphocyte leukemia (CLL), diffuse large B-cell lymphoma (DLBCL), mantle cell lymphoma, neuroblastoma, breast cancer, or ovarian cancer in a patient in need thereof, the method comprising administering ritonavir and metformin, or pharmaceutically acceptable salts thereof, wherein ritonavir and metformin are administered either before, concurrently, or after each other to the patient.

5. The method of claim 4, wherein the method further comprises administering a DNA damaging agent.

6. The method of claim 5, wherein the DNA damaging agent is selected from doxorubicin, daunorubicin, epirubicin, idarubicin, valrubicin, and mitoxantrone.

7. The method of claim 6, wherein the DNA damaging agent is doxorubicin.

8. The method of claim 4, wherein the method further comprises administering a proteasome inhibitor.

9. The method of claim 8, wherein the proteasome inhibitor is selected from bortezomib, disulfiram, epigallocatechin-3-gallate, and salinosporamide A.

10. The method of claim 9, wherein the proteasome inhibitor is bortezomib.

11. The method of claim 4, wherein the ritonavir and/or the metformin is administered after the patient has fasted for at least 4 hours.

12. The method of claim 11, wherein the ritonavir and/or the metformin is administered after the patient has fasted for at least 6 hours.

13. The method of claim 12, wherein the ritonavir and/or the metformin is administered after the patient has fasted for at least 12 hours.

* * * * *